(12) United States Patent
Ackermann et al.

(10) Patent No.: US 7,858,645 B2
(45) Date of Patent: Dec. 28, 2010

(54) INDAZOLE DERIVATIVES

(75) Inventors: Jean Ackermann, Riehen (CH);
Konrad Bleicher, Freiburg (DE);
Simona M. Ceccarelli, Basel (CH);
Odile Chomienne, Altkirch (FR);
Patrizio Mattei, Riehen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 453 days.

(21) Appl. No.: 11/875,025

(22) Filed: Oct. 19, 2007

(65) Prior Publication Data
US 2008/0103182 A1    May 1, 2008

(30) Foreign Application Priority Data
Nov. 1, 2006    (EP)    ............ 06123321

(51) Int. Cl.
*A61K 31/416*    (2006.01)
*A61K 31/4155*    (2006.01)
*A61K 31/4245*    (2006.01)
*A61K 31/4439*    (2006.01)
*C07D 231/56*    (2006.01)
*C07D 401/02*    (2006.01)
*C07D 403/02*    (2006.01)
*C07D 413/02*    (2006.01)

(52) U.S. Cl. ............ 514/338; 514/364; 514/381; 514/403; 546/275.7; 548/125; 548/253; 548/362.5

(58) Field of Classification Search ............ None
See application file for complete search history.

(56) References Cited
FOREIGN PATENT DOCUMENTS
DE    10 2004 054 666 A1    5/2006
WO    WO 2005/056532 A1    6/2005

OTHER PUBLICATIONS

Korbonits et al Journal of the Chemical Society, Perkin Transactions 1: Organic and Bio-Organic Chemistry (1982), (3), 759-66.*
Sall et al., J. Med. Chem., 40, pp. 2843-2857 (1997).
Snyder et al., J. Am. Chem. Soc., 74, pp. 2009-2012 (1952).
Jackson et al., Biochem., 341, pp. 483-489 (1999).
Jackson et al., J. Biol. Chem., 275, pp. 19560-19566 (2000).
Korbonits, D., et al., Journal of the Chemical Society, vol. 1, No. 3, pp. 759-766 (1982), XP002221091.

* cited by examiner

*Primary Examiner*—Kamal A Saeed
(74) *Attorney, Agent, or Firm*—George W. Johnston; Dennis P. Tramaloni; Brian C. Remy

(57) ABSTRACT

The invention is concerned with novel indazole derivatives of formula (I)

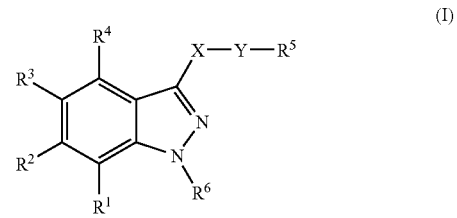

wherein $R^1$, $R^2$, $R^3$, $R^4$, $R^5$, $R^6$, X and Y are as defined in the description and in the claims, as well as physiologically acceptable salts and esters thereof. These compounds inhibit L-CPT1 and can be used in the prevention or treatment of diseases which are modulated by L-CPT1 inhibitors.

20 Claims, No Drawings

INDAZOLE DERIVATIVES

PRIORITY TO RELATED APPLICATION(S)

This application claims the benefit of European Patent Application No. 06123321.9, filed Nov. 1, 2006, which is hereby incorporated by reference in its entirety.

BACKGROUND OF THE INVENTION

The invention is concerned with novel indazole derivatives and their use as inhibitors of liver carnitine palmitoyl transferase 1 (L-CPT1).

High levels of free fatty acids (FFA) lead to an increase of liver mitochondrial β-oxidation, which is crucial to drive efficient gluconeogenesis. The mitochondrial oxidation of long-chain FFA requires the intervention of two membrane-bound carnitine-dependent palmitoyltransferases (CPTs). CPT1, the outer mitochondrial membrane enzyme, catalyzes the formation of long-chain acylcarnitines. Liver (L-CPT1) and muscle (M-CPT1) CPT1 isoforms are encoded by two different genes and inhibited by malonyl-CoA. The N-ter domain of L-CPT1 confers its lower sensitivity to malonyl CoA. CPT2, the inner mitochondrial membrane enzyme, reconverts long-chain acylcarnitines into long-chain acyl CoA esters. Long-chain acyl-CoAs are then β-oxidized to acetyl-CoA, which activates the pyruvate carboxylase and gluconeogenesis. According to the mechanism of action described above, pharmaceutically active substances which inhibit L-CPT1 reduce liver β-oxidation, consequently inhibit gluconeogenesis and therefore counteract hyperglycemia.

SUMMARY OF THE INVENTION

In sum, the present invention relates to the compounds of formula (I):

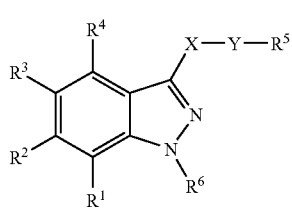

(I)

or a pharmaceutically acceptable salt thereof wherein $R^1$-$R^6$, X, and Y, are as defined in the detailed description and in the claims. The compounds of formula I inhibit liver carnitine palmitoyl transferase 1 (L-CPT1) activity.

The compounds of the present invention can be used as pharmaceutically active agents which are useful in the prevention and/or treatment of diseases which are modulated by L-CPT1 inhibitors, particularly diseases which are related to hyperglycemia and/or glucose tolerance disorders. Such diseases include e.g. diabetes and associated pathologies, non insulin dependent diabetes mellitus (also referred to as diabetes type II), obesity, hypertension, insulin resistance syndrome, metabolic syndrome, hyperlipidemia, hypercholesterolemia, fatty liver disease, atherosclerosis, congestive heart failure and renal failure. Further, the invention is concerned with a process for the manufacture of the above compounds, pharmaceutical preparations which contain such compounds as well as the use of these compounds for the production of pharmaceutical preparations.

DETAILED DESCRIPTION OF THE INVENTION

Unless otherwise indicated, the following definitions are set forth to illustrate and define the meaning and scope of the various terms used to describe the invention herein.

In this specification, the term "lower" is used to mean a group consisting of one to seven carbon atoms. In preferred embodiments, a lower group has one to four carbon atom(s).

The term "halogen" refers to fluorine, chlorine, bromine or iodine. In preferred embodiments, the halogen is fluorine, chlorine or bromine.

The term "alkyl" alone or in combination with other groups, refers to a branched or straight-chain monovalent saturated aliphatic hydrocarbon radical of one to twenty carbon atoms. In preferred embodiments, the alkyl has one to sixteen carbon atoms, and more preferably one to ten carbon atoms. Lower-alkyl groups as described below also are preferred alkyl groups. Alkyl groups can optionally be substituted with hydroxy, $NH_2$, N(H,lower-alkyl), N(lower-alkyl)$_2$ or COOH. Unsubstituted alkyl groups are preferred.

The term "lower-alkyl," alone or in combination with other groups, refers to a branched or straight-chain monovalent alkyl radical of one to seven carbon atoms. In preferred embodiments, the lower alkyl has one to four carbon atoms. This term is further exemplified by such radicals as methyl, ethyl, n-propyl, isopropyl, n-butyl, s-butyl, t-butyl and the like. Lower-alkyl groups can optionally be substituted with hydroxy, $NH_2$, N(H, lower-alkyl), N(lower-alkyl)$_2$ or COOH. Unsubstituted lower-alkyl groups are preferred.

The term "cycloalkyl" refers to a monovalent carbocyclic radical of 3 to 10 carbon atoms. In preferred embodiments, the cycloalkyl has 3 to 6 carbon atoms, such as cyclopropyl, cyclobutyl, cyclopentyl, or cyclohexyl.

The term "fluoro-lower-alkyl" refers to lower-alkyl groups which are mono- or multiply substituted with fluorine. Examples of fluoro-lower-alkyl groups are, i.e., $CFH_2$, $CF_2H$, $CF_3$, $CF_3CH_2$, $CF_3(CH_2)_2$, $(CF_3)_2CH$ and $CF_2H$—$CF_2$.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl. Examples of fluoro-lower-alkoxy groups are i.e, $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "acid isostere" refers to groups which have similar steric and electronic features of a carboxylic acid, or that are known in the art to mimic the spatial arrangement and electronic properties of a carboxylic acid. Examples of acid isosteres are 1H-tetrazol-2-yl, 4H-[1,2,4]oxadiazol-3-yl-5-one, 4H-[1,2,4]thiadiazol-3-yl-5-one, 4H-[1,2,4]oxadiazol-3-yl-5-thione, 3H-[1,2,3,5]oxathiadiazol-4-yl-2-oxide, $SO_3H$, 3-hydroxy-isooxazol, 3-hydroxy-pyran-4-one or P(O)(OCH$_2$CH$_3$)OH.

The term "aryl", alone or in combination, relates to the phenyl or naphthyl group, which can optionally be substituted, unless specifically stated otherwise, by 1 to 5 substituents, independently selected from the group consisting of halogen, hydroxy, amino, $NO_2$, lower-alkyl, hydroxy-lower-alkyl, lower-alkoxy, carboxy, carboxy-lower-alkyl, $H_2NC(O)$, (H,lower-alkyl)NC(O), (lower-alkyl)$_2$NC(O), fluoro-lower-alkyl, lower-alkyl-SO$_2$, lower-alkyl-SO$_2$O, lower-alkyl-SO$_2$—NH, lower-alkyl-SO$_2$—N(lower-alkyl), $H_2NSO_2$, (H, lower-alkyl)NSO$_2$, (lower-alkyl)$_2$NSO$_2$, cyano, heteroaryl, cycloalkyl, phenyl and phenyloxy. In preferred embodiments the aryl is a phenyl group and the number of substituents ranges from 1 to 3. Preferred substituents are halogen, lower-alkyl, fluoro-lower-alkyl, lower-alkoxy and fluoro-lower-alkoxy. Furthermore, the aryl groups can preferably be substituted as described in the description below.

The term "heteroaryl" refers to an aromatic 5 to 6 membered monocyclic ring or 9 to 10 membered bicyclic ring which can comprise 1, 2 or 3 atoms of nitrogen, oxygen or sulphur, such as, i.e., furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, indazolyl, benzoisothiazolyl, benzoxazolyl, benzoisoxazolyl and quinolinyl. Preferred heteroaryl groups are thiophenyl, pyridinyl, furanyl and thiazolyl. Unless specifically stated otherwise, a heteroaryl group may optionally have a substitution pattern as described earlier in connection with the term "aryl". Furthermore, heteroaryl groups can preferably be substituted as described in the description below.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid. The term "pharmaceutically acceptable salts" refers to such salts. Compounds of formula (I) which comprise an acid group such as COOH or an acid isostere can form salts with physiologically compatible bases. Examples of such salts are alkaline, earth-alkaline and ammonium salts such as e.g. sodium, potassium, calcium and trimethylammonium salt. The term "pharmaceutically acceptable salts" also refers to such salts.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In reference to a particular group or molecule, the term "substituted" refers to the fact that at least one of the hydrogen atoms of that group or molecule is replaced by some other substituent.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, preferably from about 0.1 mg to about 1,000 mg, more preferably from about 0.5 to 500 mg, and more preferably from about 1 mg to 300 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" means any compound selected from the genus of compounds as defined by the formula.

In detail, the present invention relates to a compound of formula (I):

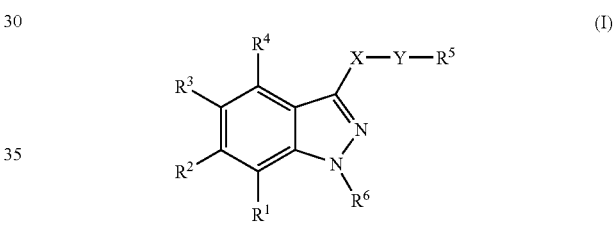

or a pharmaceutically acceptable salt or ester thereof, wherein:

X is —C(O)—NH—, —NH—C(O)—, or —(CR$^7$R$^8$)$_m$—S—, wherein R$^7$ and R$^8$ independently from each other are selected from the group consisting of hydrogen, lower-alkyl, fluoro-lower-alkyl, lower-alkoxy, and fluoro-lower-alkoxy; and m is 0 or 1;

Y is —(CR$^9$R$^{10}$)$_n$—, wherein R$^9$ and R$^{10}$ independently from each other are selected from the group consisting of hydrogen, lower alkyl, fluoro-lower-alkyl, lower-alkoxy, and fluoro-lower-alkoxy; and n is 0 or 1;

R$^1$, R$^2$, R$^3$ and R$^4$ independently from each other are selected from the group consisting of:
(1) hydrogen,
(2) halogen,
(3) lower-alkyl,
(4) fluoro-lower-alkyl,
(5) lower-alkoxy,
(6) fluoro-lower-alkoxy,
(7) carbamoyl,
(8) lower-alkyl-NH—C(O)—NH,
(9) aryl-lower-alkyl-NH—C(O)—NH, and
(10) lower-alkyl-SO$_2$—NH-lower-alkyl;

R$^5$ is phenyl or a heteroaryl selected from the group consisting of (a) thiophenyl, (b) pyridinyl, (c) furanyl, and (d) thiazolyl, which phenyl or heteroaryl is optionally substituted with 1 to 3 substituents independently selected from the group consisting of:
(1) halogen,
(2) lower-alkyl,
(3) fluoro-lower-alkyl,
(4) lower-alkoxy,
(5) fluoro-lower-alkoxy,
(6) hydroxy,
(7) HO—$SO_2$,
(8) $NH_2$—$SO_2$,
(9) N(H,lower-alkyl)-$SO_2$,
(10) N(lower-alkyl)$_2$-$SO_2$,
(11) lower-alkyl-$SO_2$—NH,
(12) carboxy,
(13) carboxy-lower-alkyl,
(14) carboxy-lower-alkoxy,
(15) $NO_2$,
(16) CN,
(17) $NH_2$,
(18) N(H,lower-alkyl),
(19) N(lower-alkyl)$_2$,
(20) $NH_2$C(O),
(21) N(H,lower-alkyl)C(O),
(22) N(lower-alkyl)$_2$C(O),
(23) lower-alkyl-C(O)NH,
(24) 1H-tetrazol-5-yl and
(25) 5-oxo-4,5-dihydro-[1,2,4]oxadiazol-3-yl;

$R^6$ is $C_{2-7}$-alkyl or

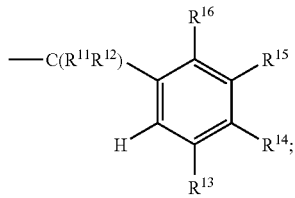

wherein: (a) $R^{11}$ and $R^{12}$ independently from each other are selected from the group consisting of hydrogen, lower-alkyl, fluoro-lower-alkyl, lower-alkoxy, and fluoro-lower-alkoxy; (b) $R^{13}$, $R^{14}$ and $R^{15}$ independently from each other are selected from the group consisting of hydrogen, lower-alkyl, halogen, fluoro-lower-alkyl, lower-alkoxy, hydroxy, fluoro-lower-alkoxy, $NO_2$ or $NH_2$—C(O); and (c) $R^{16}$ is hydrogen or lower-alkoxy;

with the proviso that the compound of formula (I) is not:
N-[1-(phenylmethyl)-1H-indazol-3-yl]-benzamide,
4-methyl-N-[1-(phenylmethyl)-1H-indazol-3-yl]-benzamide,
4-nitro-N-[1-(phenylmethyl)-1H-indazol-3-yl]-benzamide,
4-chloro-N-[1-(phenylmethyl)-1H-indazol-3-yl]-benzamide,
4-methoxy-N-[1-(phenylmethyl)-1H-indazol-3-yl]-benzamide,
N-[1-(phenylmethyl)-1H-indazol-3-yl]-benzenacetamide, or
N-(1-ethyl-1H-indazol-3-yl)-benzamide.

Compounds of formula (I) are individually preferred and physiologically acceptable salts thereof are individually preferred and pharmaceutically acceptable esters thereof are individually preferred, with the compounds of formula (I) being particularly preferred.

N-[1-(phenylmethyl)-1H-indazol-3-yl]-benzenacetamide is also known as N-[1-(phenylmethyl)-1H-indazol-3-yl]-benzeneacetamide.

The compounds of formula (I) can have one or more asymmetric carbon or sulfur atoms and can therefore exist as an enantiomeric mixture, mixture of stereoisomers or as optically pure compounds.

A preferred embodiment of the present invention relates to compounds of formula (I) as described above, wherein X is —C(O)—NH— or —NH—C(O)—. Compounds in which X is —C(O)—NH— or —NH—C(O)— individually constitute separate preferred embodiments of the present invention.

Other preferred compounds of the present invention are those, wherein $R^1$, $R^2$, $R^3$ and $R^4$ independently from each other are hydrogen, halogen, carbamoyl, lower-alkyl-NH—C(O)—NH, aryl-lower-alkyl-NH—C(O)—NH or lower-alkyl-$SO_2$—NH-lower-alkyl. Preferably, $R^1$, $R^2$, $R^3$ and $R^4$ independently from each other are hydrogen or halogen. More preferably, $R^1$ is hydrogen. It is also preferred, that $R^2$ is hydrogen. Furthermore, it is preferred that $R^3$ is hydrogen or fluoro. In addition, it is preferred that $R^4$ is hydrogen.

Another preferred embodiment of the present invention is related to compounds of formula (I) as described above, wherein $R^5$ is phenyl or heteroaryl selected from the group consisting of thiophenyl, pyridinyl, furanyl and thiazolyl, which phenyl or heteroaryl is optionally substituted with 1 to 3 substituents independently selected from the group consisting of halogen, lower-alkyl, lower-alkoxy, carboxy, carboxy-lower-alkyl, carboxy-lower-alkoxy, 1H-tetrazol-5-yl and 5-oxo-4,5-dihydro-[1,2,4]oxadiazol-3-yl. Phenyl and heteroaryl individually constitute separate preferred embodiments of the present invention. More preferably, $R^5$ is phenyl or thiophenyl, which phenyl or thiophenyl is optionally substituted with 1 to 3 substituents independently selected from the group consisting of halogen, lower-alkoxy, carboxy and 1H-tetrazol-5-yl. It is particularly preferred that $R^5$ is 4-carboxy-phenyl, thiophenyl, phenyl, 3-fluoro-phenyl, 3-methoxy-phenyl or 4-(1H-tetrazol-5-yl)-phenyl.

Other preferred compounds of the present invention are those, wherein $R^6$ is

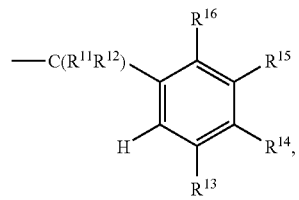

and $R^{11}$, $R^{12}$, $R^{13}$, $R^{14}$, $R^{15}$ and $R^{16}$ are as defined above.

Preferred compounds of formula (I) as described above are those wherein $R^7$ is hydrogen. Other preferred compounds are those, wherein $R^8$ is hydrogen. Other preferred compounds are those, wherein $R^9$ is hydrogen. It is also preferred that $R^{10}$ is hydrogen. Furthermore, it is preferred that $R^{11}$ is hydrogen. Compounds in which $R^{12}$ is hydrogen are also preferred.

In a preferred embodiment of the present invention, $R^{13}$, $R^{14}$ and $R^{15}$ independently from each other are hydrogen, halogen, fluoro-lower-alkyl, lower-alkoxy, fluoro-lower-alkyl, $NO_2$ or $NH_2$—C(O). Preferably, $R^{13}$, $R^{14}$ and $R^{15}$ independently from each other are hydrogen, halogen, fluoro-lower-alkyl, fluoro-lower-alkoxy or $NH_2$—C(O). More preferably, $R^{13}$ is hydrogen, trifluoromethyl or chloro. It is also preferred that $R^{14}$ is hydrogen, difluoromethoxy or $NH_2$—C(O). Preferably, $R^{15}$ is hydrogen. Furthermore, it is preferred that $R^{16}$ is hydrogen.

Other preferred compounds are those, wherein m is 1. Compounds in which n is 0 or 1, individually constitute separate preferred embodiments of the present invention.

In particular, preferred compounds are the compounds of formula (I) described in the examples as individual compounds as well as pharmaceutically acceptable salts as well as pharmaceutically acceptable esters thereof. Furthermore, the substituents as found in the specific examples described below, individually constitute separate preferred embodiments of the present invention.

Preferred compounds of formula (I) are those selected from the group consisting of:

N-[1-(4-Difluoromethoxy-benzyl)-1H-indazol-3-yl]-terephthalamic acid,
N-[1-(4-Difluoromethoxy-benzyl)-1H-indazol-3-yl]-benzamide,
Thiophene-2-carboxylic acid [1-(4-difluoromethoxy-benzyl)-1H-indazol-3-yl]-amide,
N-[1-(4-Difluoromethoxy-benzyl)-1H-indazol-3-yl]-3-fluoro-benzamide,
N-[1-(4-Difluoromethoxy-benzyl)-1H-indazol-3-yl]-3-methoxy-benzamide,
N-[1-(4-Difluoromethoxy-benzyl)-1H-indazol-3-yl]-isonicotinamide,
N-[1-(4-Difluoromethoxy-benzyl)-5-fluoro-1H-indazol-3-yl]-terephthalamic acid,
N-[1-(4-Difluoromethoxy-benzyl)-5-fluoro-1H-indazol-3-yl]-benzamide,
N-[1-(4-Difluoromethoxy-benzyl)-5-fluoro-1H-indazol-3-yl]-3-fluoro-benzamide,
Thiophene-2-carboxylic acid [1-(4-difluoromethoxy-benzyl)-5-fluoro-1H-indazol-3-yl]-amide,
N-[1-(4-Difluoromethoxy-benzyl)-5-fluoro-1H-indazol-3-yl]-3-methoxy-benzamide,
N-[1-(4-Difluoromethoxy-benzyl)-5-fluoro-1H-indazol-3-yl]-isonicotinamide,
N-[1-(4-Difluoromethoxy-benzyl)-5-fluoro-1H-indazol-3-yl]-nicotinamide,
N-[1-(3-Chloro-benzyl)-5-fluoro-1H-indazol-3-yl]-terephthalamic acid,
N-[1-(3-Chloro-benzyl)-5-fluoro-1H-indazol-3-yl]-benzamide,
N-[1-(3-Chloro-benzyl)-5-fluoro-1H-indazol-3-yl]-3-fluoro-benzamide,
N-[1-(3-Chloro-benzyl)-5-fluoro-1H-indazol-3-yl]-3-methoxy-benzamide,
Thiophene-2-carboxylic acid [1-(3-chloro-benzyl)-5-fluoro-1H-indazol-3-yl]-amide,
Furan-2-carboxylic acid [1-(3-chloro-benzyl)-5-fluoro-1H-indazol-3-yl]-amide,
N-[1-(4-Difluoromethoxy-benzyl)-7-fluoro-1H-indazol-3-yl]-terephthalamic acid,
N-[1-(3-Chloro-benzyl)-7-fluoro-1H-indazol-3-yl]-terephthalamic acid,
Thiophene-2-carboxylic acid [1-(3-chloro-benzyl)-7-fluoro-1H-indazol-3-yl]-amide,
N-[1-(3-Chloro-benzyl)-6-fluoro-1H-indazol-3-yl]-terephthalamic acid,
Thiophene-2-carboxylic acid [1-(4-difluoromethoxy-benzyl)-6-fluoro-1H-indazol-3-yl]-amide,
Thiophene-2-carboxylic acid (1-benzyl-1H-indazol-3-yl)-amide,
1-Ethyl-5-(3-propyl-ureido)-1H-indazole-3-carboxylic acid (thiophen-2-ylmethyl)-amide,
1-Ethyl-5-(3-isopropyl-ureido)-1H-indazole-3-carboxylic acid (thiophen-2-ylmethyl)-amide,
1-Ethyl-5-(3-phenethyl-ureido)-1H-indazole-3-carboxylic acid (thiophen-2-ylmethyl)-amide,
1-Ethyl-5-(3-ethyl-ureido)-1H-indazole-3-carboxylic acid (thiophen-2-ylmethyl)-amide,
1-(4-Nitro-benzyl)-1H-indazole-3-carboxylic acid (pyridin-3-ylmethyl)-amide,
1-(4-Difluoromethoxy-benzyl)-1H-indazole-3-carboxylic acid (thiophen-2-ylmethyl)-amide,
1-(3-Trifluoromethyl-benzyl)-1H-indazole-3-carboxylic acid (thiophen-2-ylmethyl)-amide,
4-({[1-(4-Difluoromethoxy-benzyl)-5-fluoro-1H-indazole-3-carbonyl]-amino}-methyl)-benzoic acid,
(2-{[1-(4-Difluoromethoxy-benzyl)-5-fluoro-1H-indazole-3-carbonyl]-amino}-thiazol-4-yl)-acetic acid,
1-(4-Difluoromethoxy-benzyl)-5-fluoro-1H-indazole-3-carboxylic acid [4-(1H-tetrazol-5-yl)-phenyl]-amide,
1-(4-Difluoromethoxy-benzyl)-5-fluoro-1H-indazole-3-carboxylic acid 4-(1H-tetrazol-5-yl)-benzylamide,
(4-{[1-(4-Difluoromethoxy-benzyl)-5-fluoro-1H-indazole-3-carbonyl]-amino}-2-methyl-phenoxy)-acetic acid,
1-(4-Difluoromethoxy-benzyl)-5-fluoro-1H-indazole-3-carboxylic acid [4-(5-oxo-4,5-dihydro-[1,2,4]oxadiazol-3-yl)-phenyl]-amide,
4-{[5-Fluoro-1-(3-trifluoromethyl-benzyl)-1H-indazole-3-carbonyl]-amino}-benzoic acid,
5-Fluoro-1-(3-trifluoromethyl-benzyl)-1H-indazole-3-carboxylic acid [4-(1H-tetrazol-5-yl)-phenyl]-amide,
5-Fluoro-1-(3-trifluoromethyl-benzyl)-1H-indazole-3-carboxylic acid 4-(1H-tetrazol-5-yl)-benzylamide,
1-(4-Carbamoyl-benzyl)-1H-indazole-3-carboxylic acid 4-(1H-tetrazol-5-yl)-benzylamide,
1-(4-Carbamoyl-benzyl)-5-fluoro-1H-indazole-3-carboxylic acid 4-(1H-tetrazol-5-yl)-benzylamide,
1-(5-Chloro-2-methoxy-benzyl)-5-fluoro-3-[4-(1H-tetrazol-5-yl)-phenylsulfanylmethyl]-1H-indazole,
1-(4-Difluoromethoxy-benzyl)-1H-indazole-3,6-dicarboxylic acid 6-amide 3-[4-(1H-tetrazol-5-yl)-benzylamide], and
1-(4-Difluoromethoxy-benzyl)-6-(methanesulfonylamino-methyl)-1H-indazole-3-carboxylic acid [4-(1H-tetrazol-5-yl)-phenyl]-amide, and pharmaceutically acceptable salts and esters thereof.

Particularly preferred compounds of formula (I) are those selected from the group consisting of:

N-[1-(4-Difluoromethoxy-benzyl)-1H-indazol-3-yl]-terephthalamic acid,
N-[1-(4-Difluoromethoxy-benzyl)-5-fluoro-1H-indazol-3-yl]-terephthalamic acid,
N-[1-(4-Difluoromethoxy-benzyl)-5-fluoro-1H-indazol-3-yl]-benzamide,
N-[1-(4-Difluoromethoxy-benzyl)-5-fluoro-1H-indazol-3-yl]-3-fluoro-benzamide,
Thiophene-2-carboxylic acid [1-(4-difluoromethoxy-benzyl)-5-fluoro-1H-indazol-3-yl]-amide,
N-[1-(4-Difluoromethoxy-benzyl)-5-fluoro-1H-indazol-3-yl]-3-methoxy-benzamide,
N-[1-(3-Chloro-benzyl)-5-fluoro-1H-indazol-3-yl]-terephthalamic acid,
Thiophene-2-carboxylic acid [1-(3-chloro-benzyl)-5-fluoro-1H-indazol-3-yl]-amide,
1-(3-Trifluoromethyl-benzyl)-1H-indazole-3-carboxylic acid (thiophen-2-ylmethyl)-amide, and
1-(4-Carbamoyl-benzyl)-1H-indazole-3-carboxylic acid 4-(1H-tetrazol-5-yl)-benzylamide, and pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises reacting a compound of formula (VII)

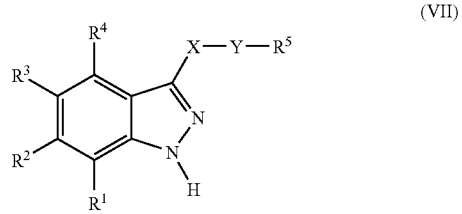

(VII)

with a compound of formula hal-R$^6$, wherein R$^1$, R$^2$, R$^3$, R$^4$, R$^5$, R$^6$, X and Y are as defined above, and hal is selected from the group consisting of chloro, bromo and iodo.

The reaction of a compound of formula (VII) with a compound of formula hal-R$^6$ can be carried out under conditions well known to the person skilled in the art. For example, the compound of formula (VII) is reacted with a compound of formula hal-R$^6$, e.g. a benzyl halogenide derivative, in a nucleophilic substitution reaction, using methods well known to someone skilled in the art. As halogenides, bromides, iodides or chlorides can be used. The reaction can be carried out at temperature between room temperature and 200° C., optionally under microwave irradiation, in various solvents, preferably polar aprotic solvents such as acetone, dimethylformamide, dimethylsulfoxide and the like. A base can conveniently be added. As bases, both organic and inorganic bases can be used, such as for example potassium tert-butylate, sodium hydride, potassium carbonate, cesium carbonate or others.

The present invention also relates to compounds of formula (I) as defined above, when prepared by a process as described above.

The compounds of formula (VII) and hal-R$^6$ can be prepared by methods known in the art or as described below or in analogy thereto. Unless otherwise indicated, R$^1$, R$^2$, R$^3$, R$^4$, R$^5$, R$^6$, X and Y are as described above.

Compounds of formula I, wherein X is —NH—C(O)— are part of the present invention and are represented by general formula II

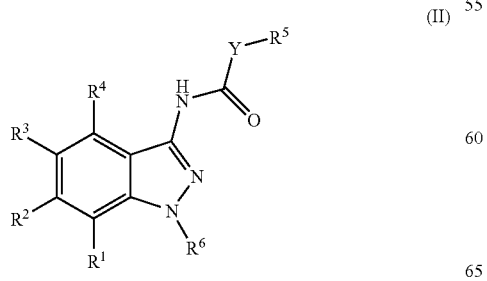

(II)

Compounds of general formula II can be accessed according to the following general scheme 1:

Scheme 1

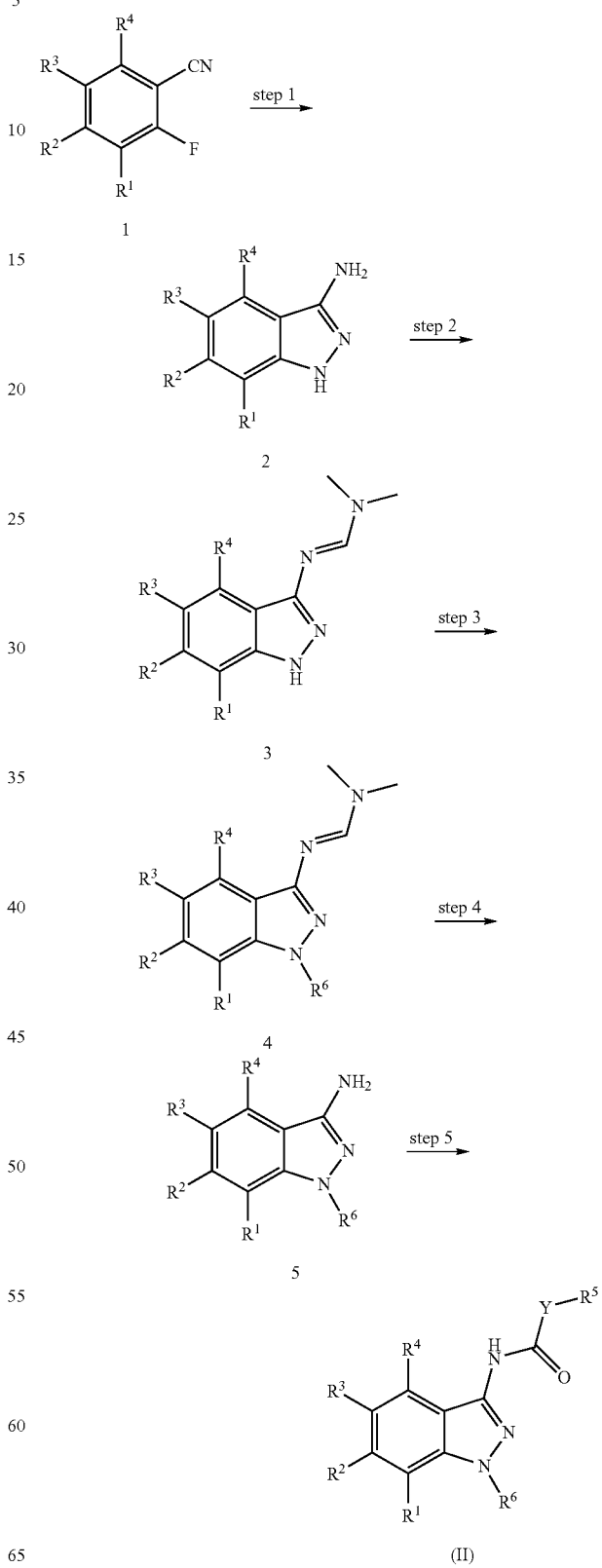

In step 1, scheme 1, a 2-fluorobenzonitrile 1 is reacted with hydrazine to produce a 3-amino-indazole 2, according to methods well known to those skilled in the art. This involves treating the 2-fluorobenzonitrile with hydrazine or hydrazine hydrate at temperatures between 0° C. and 200° C. The reaction can be carried out in the absence of solvent or in the presence of an alcoholic solvents like ethanol, butanol or other alcoholic solvents.

In step 2, scheme 1, the free amino group of 3-amino-indazole 2 is protected to the corresponding formamidino derivative 3. This involves reacting the amino indazole 2 with a formamide equivalent, for example with dimethylformamide dimethylacetal, chloromethylene-dimethyl-ammonium chloride and the like. The reaction is usually carried out without solvent or in an alcoholic solvent, as for example methanol or ethanol, at temperatures between 0° C. and 100° C.

In step 3, scheme 1, the protected 3-amino-indazole 2 is reacted with a benzyl or alkyl halogenide in a nucleophilic substitution reaction, using methods well known to someone skilled in the art. As alkyl or benzyl halogenides, alkyl- or benzyl-bromides, iodides or chlorides can be used. The reaction can be carried out at temperature between room temperature and 200° C., optionally under microwave irradiation, in various solvents, preferably polar aprotic solvents such as acetone, dimethylformamide, dimethylsulfoxide and the like. As bases, both organic and inorganic bases can be used, such as for example potassium tert-butylate, sodium hydride, potassium carbonate, cesium carbonate or others.

In step 4, scheme 1, the formamidine protective group is removed to yield the free 3-aminoindazole 5 according to methods well known to someone skilled in the art, for example by treatment with a base like hydrazine hydrate, sodium hydroxide or other in alcoholic solvent at room temperature.

In step 5, scheme 1, the amino group of 3-aminoindazoles 5 is converted, with the appropriate acid $R^5$–Y–$CO_2H$, into the corresponding product of general formula II, using methods well known to someone skilled in the art e.g. amide formation using a coupling reagent. The reaction is typically carried out in aprotic solvents such as dichloromethane, tetrahydrofuran, N,N-dimethylformamide, N-methylpyrrolidinone and mixtures thereof at temperatures between 0° C. and 80° C. in the presence or absence of a base such as triethylamine, diisopropylethylamine, 4-methylmorpholine, and/or 4-(dimethylamino)pyridine. Typically used coupling agents are N,N'-dicyclohexylcarbodiimide, 1-(3-dimethylamino-propyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate and bromo-tris-pyrrolidino-phosphonium hexafluorophosphate. Alternatively, such reaction can be performed by coupling the amino group of 3-aminoindazoles 5 with an appropriate acyl halide, typically an acyl chloride of general formula $R^5$–Y–COCl in the presence of a base. The reaction is generally conducted in an aprotic solvent, like dichloromethane, tetrahydrofuran or acetone, in the presence of a base. Typical bases are triethylamine, 4-methylmorpholine, pyridine, diisopropylethylamine or 4-(dimethylamino)pyridine or mixtures thereof. Solid phase bound bases, like for example polystyrene bound carbonate can be used. Occasionally, double acylation of the amino group of 3-aminoindazoles 5 is observed. In such cases, the diacylated product can be reconverted to the desired product II by treatment with a base, typically aqueous NaOH, KOH or LiOH. Solid phase bound bases, like for example solid phase bound diethylenetriamine can also be used.

Compounds of formula I where X is —C(O)—NH— are part of the present invention and are represented by general formula III

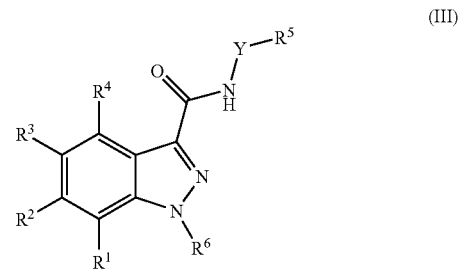

Compounds of general formula III can be accessed according to the following general scheme 2:

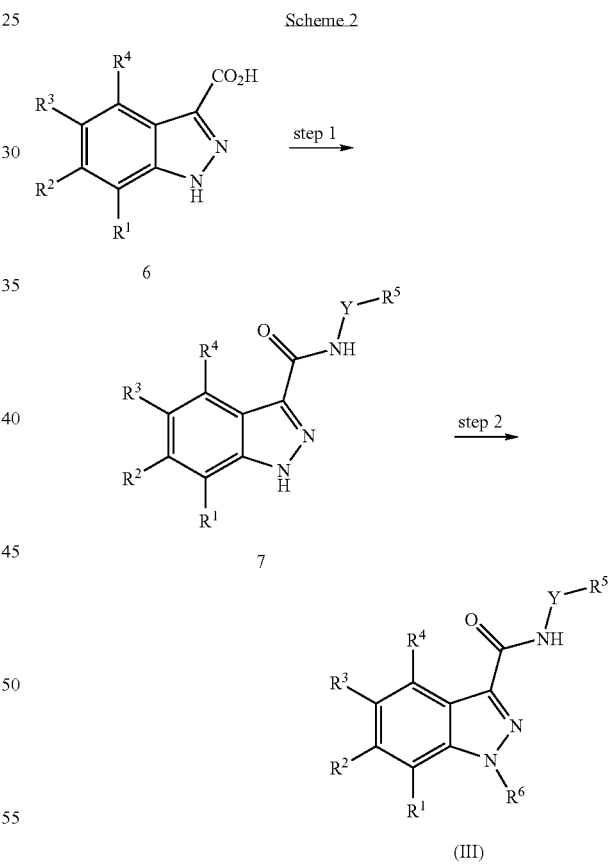

In step 1, scheme 2, indazole-3-carboxylic acids 6 are converted, with the appropriate amine $R^5$–Y–$NH_2$, into the corresponding amides of general formula 7, using methods well known to someone skilled in the art, e.g. amide formation using a coupling reagent. The reaction is typically carried out in aprotic solvents such as dichloromethane, tetrahydrofuran, N,N-dimethylformamide, N-methylpyrrolidinone and mixtures thereof at temperatures between 0° C. and 80° C. in the presence or absence of a base such as triethylamine, diisopropylethylamine, 4-methylmorpholine, and/or 4-(dimethylamino)pyridine. Typically used coupling agents are N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate and bromo-tris-pyrrolidino-phosphonium hexafluorophosphate. Alternatively, such reaction can be performed in two steps involving first formation of the acyl halide derivative of 6 and subsequent coupling reaction with an appropriate amine in the presence of a base. Typically employed reagents for the formation of the acyl chloride are thionyl chloride, phosphorous pentachloride, oxalyl chloride, (1-chloro-2-methyl-propenyl)-dimethyl-amine or cyanuric chloride, and the reaction is generally conducted in the absence of a solvent or in the presence of an aprotic solvent like dichloromethane, toluene or acetone. A base can optionally be added, like for example pyridine, triethylamine, diisopropylethylamine or 4-methylmorpholine. The obtained acyl chloride can be isolated or reacted as such with amine $R^5$—Y—$NH_2$ in an aprotic solvent, like dichloromethane, tetrahydrofuran or acetone, in the presence of a base. Typical bases are triethylamine, 4-methylmorpholine, pyridine, diisopropylethylamine or 4-(dimethylamino)pyridine or mixtures thereof.

In step 2, scheme 2, the indazole-3-carboxylic acid amides are reacted at the free indazole NH with a benzyl or alkyl halogenide in a nucleophilic substitution reaction, using methods well known to someone skilled in the art. As alkyl or benzyl halogenides, alkyl- or benzyl-bromides, iodides or chlorides can be used. The reaction can be carried out at temperature between room temperature and 200° C., optionally under microwave irradiation, in various solvents, preferably polar aprotic solvents such as acetone, dimethylsulfoxide and the like. As bases, both organic and inorganic bases can be used, such as for example potassium tert-butylate, sodium hydride, potassium carbonate, cesium carbonate or others.

Alternatively, compounds of general formula III can be accessed according to the following general scheme 3:

Scheme 3

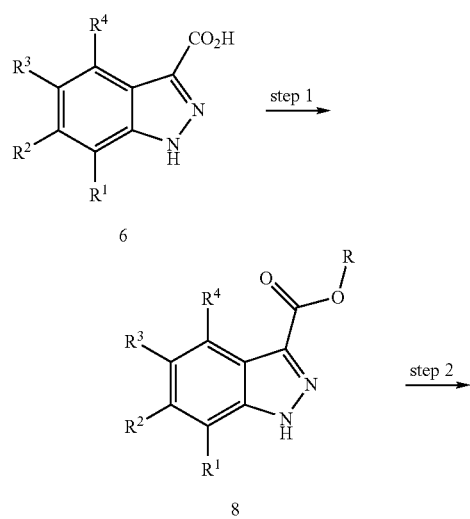

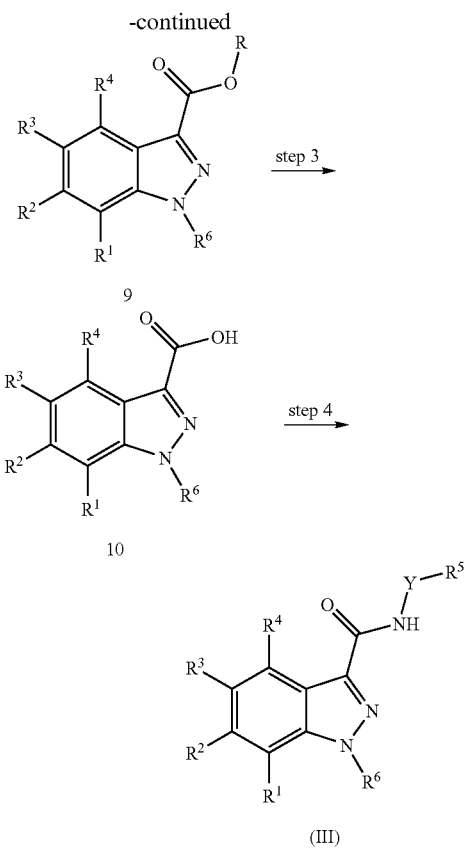

R = Me, Et, $(CH_3)_3SiCH_2CH_2^-$

In step 1, scheme 3, the carboxylic acid group of indazole-3-carboxylic acids 6, is protected according to methods well known to someone skilled in the art, e.g. via ester formation. The reaction is performed by treated the indazole-3-carboxylic acids 6 with an appropriate alcohol in the presence of a coupling agent. The reaction is typically carried out in aprotic solvents such as dichloromethane, tetrahydrofuran, N,N-dimethylformamide, N-methylpyrrolidinone and mixtures thereof at temperatures between 0° C. and 80° C. in the presence or absence of a base such as triethylamine, diisopropylethylamine, 4-methylmorpholine, and/or 4-(dimethylamino)pyridine. Typically used coupling agents are N,N'-dicyclohexylcarbodiimide, carbonyldiimidazole, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N', N'-tetramethyluronium hexafluoro-phosphate and bromo-tris-pyrrolidino-phosphonium hexafluorophosphate. Alternatively, the reaction can be performed by treating a mixture of the acid 6 and the desired alcohol with a mineral acid, like for example anhydrous hydrochloric acid or concentrated sulfuric acid. The reaction is typically carried out at temperatures between 0° C. and a 100° C. and the desired alcohol is used as solvent. As alcohols, methanol, ethanol and 2-trimethylsilylethanol can be used.

In step 2, scheme 3, the indazole-3-carboxylic acid esters 8 are reacted at the free indazole NH with a benzyl or alkyl halogenide in a nucleophilic substitution reaction, using methods well known to someone skilled in the art. As alkyl or benzyl halogenides, alkyl- or benzyl-bromides, iodides or chlorides can be used. The reaction can be carried out at temperature between room temperature and 200° C., optionally under microwave irradiation, in various solvents, preferably polar aprotic solvents such as acetone, dimethylsulfoxide and the like. As bases, both organic and inorganic bases can be used, such as for example potassium tert-butylate, sodium hydride, potassium carbonate, cesium carbonate or others.

In step 3, scheme 3, the indazole-3-carboxylic acid esters 9 are converted into the corresponding carboxylic acids of the formula 10, using methods well known to someone skilled in the art, e.g. base mediated ester hydrolysis. The reaction is typically carried out in solvents such as water, methanol, ethanol, tetrahydrofuran and mixtures thereof at temperatures between −20° C. and 120° C. Typical reagents are aqueous or anhydrous lithium hydroxide, lithium hydroxide monohydrate, sodium hydroxide, potassium hydroxide, sodium hydrogen carbonate, sodium carbonate, potassium hydrogen carbonate and potassium carbonate. In the case where R is 2-trimethylsilylethyl, the hydrolysis reaction can be performed using a fluoride source instead than an aqueous base. The reaction is carried out in an organic solvent, like for example dichloromethane, tetrahydrofuran, N,N-dimethylformamide, at temperatures between −10° C. and 100° C. Typically used fluoride sources are tetrabutylammonium fluoride, hydrogen fluoride-pyrdine and hydrofluoric acid, as well as others well known to someone skilled in the art.

In step 4, scheme 3, indazole-3-carboxylic acids 10 are converted, with the appropriate amine $R^5$—Y—$NH_2$, into the corresponding amides of general formula III, in analogy to what described in scheme 2, step 1.

Compounds of formula I where X is —$CH_2$—S— are part of the present invention and are represented by general formula IV:

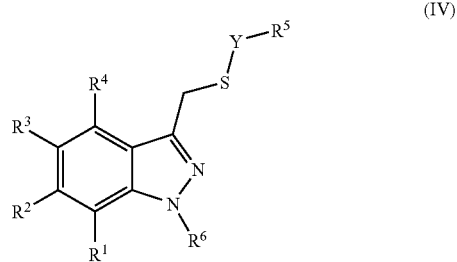

Compounds of general formula IV can be accessed according to the following general scheme 4:

Scheme 4

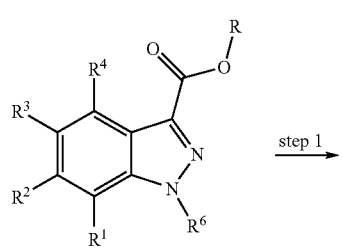

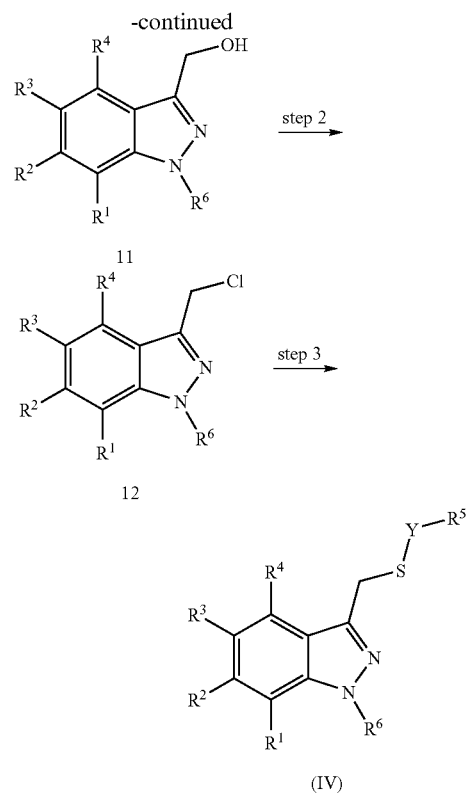

R = Me, Et, $(CH_3)_3SiCH_2CH_2$-

In step 1, scheme 4, the already described indazole-3-carboxylic acid esters 9 are converted to the corresponding (indazol-3-yl)-methanol derivatives 11 according to methods well known to someone skilled in the art e.g. via ester reduction. The reaction is typically carried out in an aprotic solvent, as for example tetrahydrofuran, diethyl ether or the like, at temperatures between −10° C. and 25° C. Typically employed reducing agents are diborane, sodium borohydride, lithium borohydride, diisobutylaluminium hydride, lithium aluminium hydride and others well known to someone skilled in the art.

In step 2, scheme 4, the (indazol-3-yl)-methanol derivatives 11 are converted to the corresponding chlorides 12 according to methods well known to someone skilled in the art. The reaction is carried out in the absence of solvent or in the presence of an aprotic solvent like methylene chloride, chloroform, carbon tetrachloride and the like. Typically used reagents are phosphorous pentachloride, thionyl chloride and others well known in the art.

In step 3, scheme 4, the 3-chloromethyl-indazole derivatives 12 are converted to compounds of general formula IV according to methods well known to someone skilled in the art, e.g. nucleophilic substitution with an appropriate thiol derivative $R^5$—Y—SH. The reaction is typically carried out in a polar aprotic solvent, as for example tetrahydrofuran, acetone, acetonitrile, dimethylformamide, dimethylsulfoxide or the like, at temperatures between −10° C. and 100° C. in the presence of a base. Typically used bases are organic or inorganic bases like for example potassium tert-butylate, sodium hydride, potassium carbonate, cesium carbonate or others.

The compounds of general formula 6 which are necessary for the preparation of compounds of general formula II, III and IV can be accessed according to the following general scheme 5:

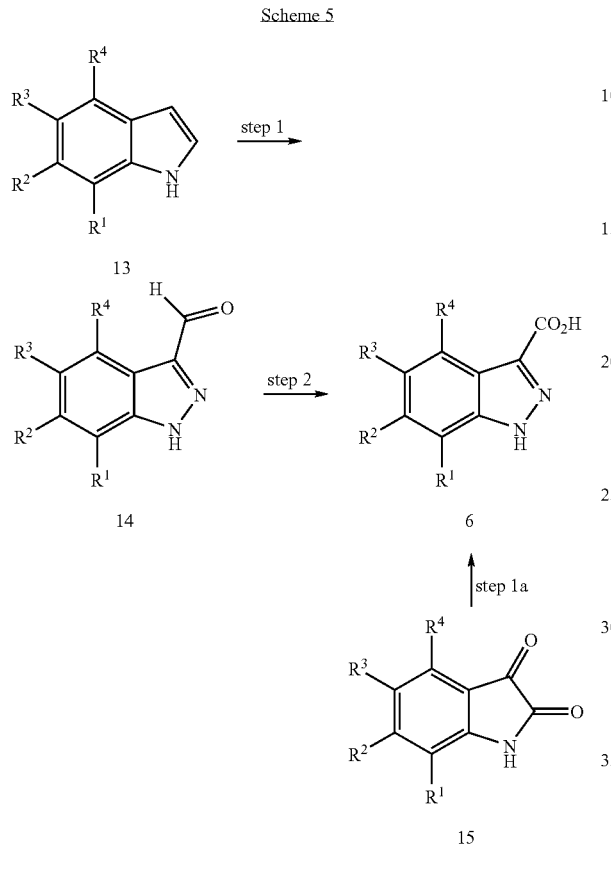

Compounds of formula I where X is —C(O)—NH— and R³ is lower-alkyl-NH—C(O)—NH— or aryl-lower-alkyl-NH—C(O)—NH— are part of the present invention and are represented by general formula V

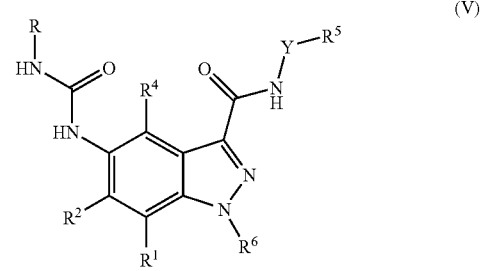

Compounds of general formula V can be accessed according to the following general scheme 6:

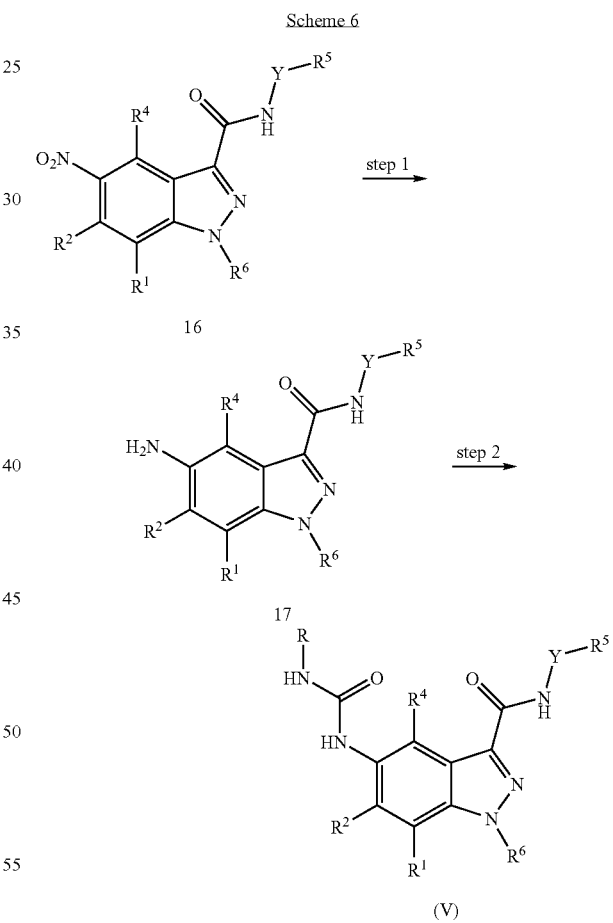

In step 1, scheme 5, indole derivatives 13, which are commercially available, or prepared according to methods well known in the art are converted to the corresponding 1H-indazole-3-carbaldehydes 14 according to the method described in J. Med. Chem. 1997, 2843. This involves treatment of the indole 13 with aqueous sodium nitrite in acidic medium, for example in aqueous hydrochloric acid.

In step 2, scheme 5, the 1H-indazole-3-carbaldehydes 14 are converted to the corresponding 1H-indazole-3-carboxylic acids 6 according to methods well known to someone skilled in the art e.g. aldehyde oxidation. The reaction can be carried out under a variety of methods and conditions. Typically used reagents are buffered sodium chlorite, acidic potassium dichromate, hydrogen peroxide, or other adequate oxidizing agents well known in the art.

Alternatively, 1H-indazole-3-carboxylic acids 6 are prepared directly from isatines 15 according to the multistep methodology described in J. Am. Chem. Soc. 1952, 2009. This involves treatment of the isatines 15 with an aqueous base, as for example sodium hydroxide, followed by diazotization of the free amine with sodium nitrite in acidic medium, as for example aqueous sulfuric or hydrochloric acid. The diazonium salt is then reduced with tin(II) chloride in acidic media to the corresponding hydrazine, which cyclizes to form the desired 1H-indazole-3-carboxylic acids 6.

In step 1, scheme 6, 5-nitro-indazole-3-carboxylic acid amides of formula 16, which can be obtained according to any of the methods described in the schemes above, are converted to the corresponding 5-amino-indazole-3-carboxylic acid amides 17 according to methods well known to someone skilled in the art e.g. nitro reduction. The reaction is typically carried out using reducing metals like iron or tin, in a solvent such as methanol, ethanol, acetic acid, water, or mixtures thereof, optionally in the presence of an acid such as ammonium chloride, hydrochloric acid, or sulfuric acid, at temperatures of 20-100° C.

In step 2, scheme 6, the 5-amino-indazole-3-carboxylic acid amides 17 are converted to the products of general formula V according to methods well known to someone skilled in the art e.g. urea formation. Typically used reagent is an adequate alkyl or aryl isocyanate. The reaction can be conducted in an aprotic solvent, like for example dichloromethane, dimethylformamide, acetonitrile and the like, in the presence of a base like for example triethylamine, diisopropylethylamine, N-methylmorfoline, and the like.

Compounds of formula I where X is —C(O)—NH— and R² is lower-alkyl-SO₂—NH-lower-alkyl are part of the present invention and are represented by general formula VI

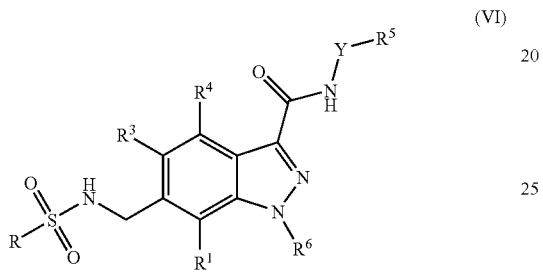

(VI)

Compounds of general formula VI can be accessed according to the following general scheme 7:

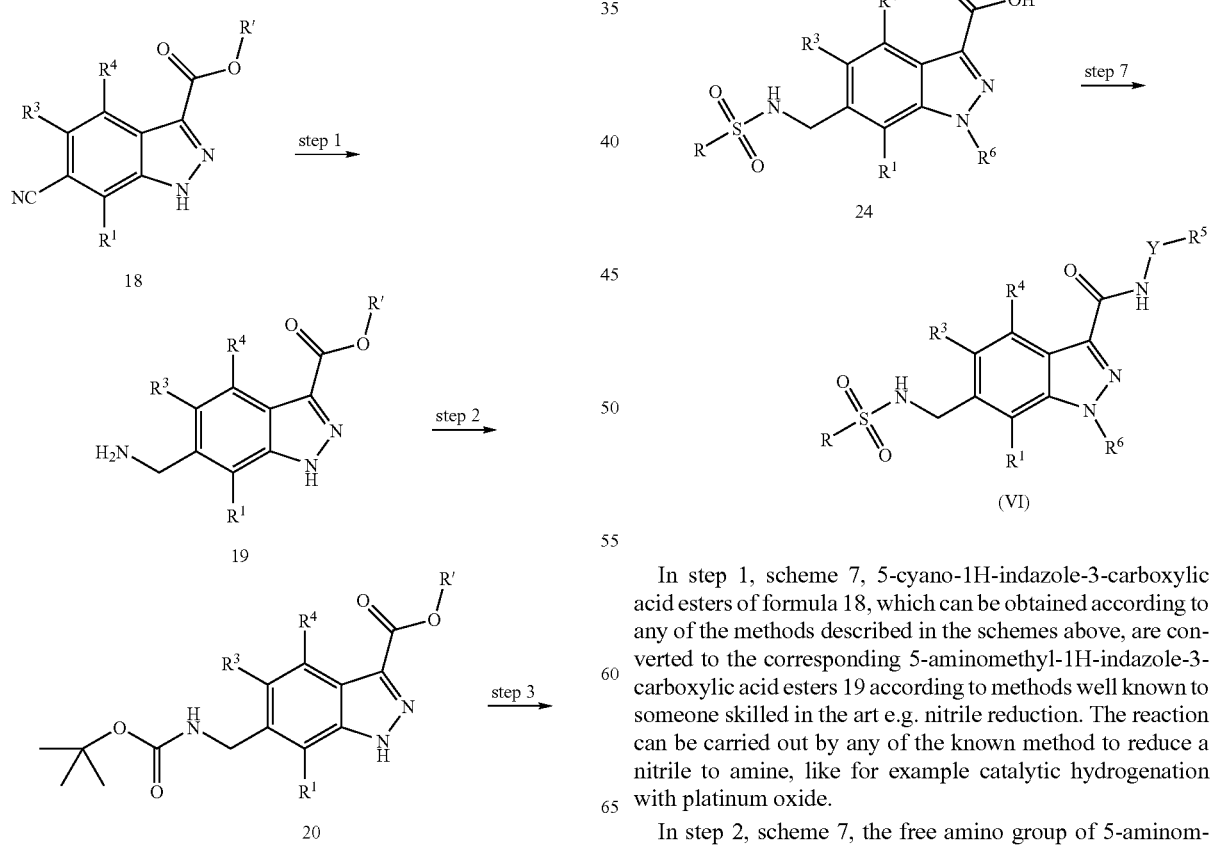

In step 1, scheme 7, 5-cyano-1H-indazole-3-carboxylic acid esters of formula 18, which can be obtained according to any of the methods described in the schemes above, are converted to the corresponding 5-aminomethyl-1H-indazole-3-carboxylic acid esters 19 according to methods well known to someone skilled in the art e.g. nitrile reduction. The reaction can be carried out by any of the known method to reduce a nitrile to amine, like for example catalytic hydrogenation with platinum oxide.

In step 2, scheme 7, the free amino group of 5-aminomethyl-1H-indazole-3-carboxylic acid esters 19 is protected with a tert-butoxycarbonyl group, according to methods well known to someone skilled in the art, e.g. by reacting the amine with di-tert-butyldicarbonate in the presence of a base, like for example triethylamine, diisopropylethylamine or other organic or inorganic bases.

In step 3, scheme 7, the protected 5-aminomethyl-1H-indazole-3-carboxylic acid esters 20 are reacted at the free indazole NH with a benzyl or alkyl halogenide in a nucleophilic substitution reaction, in analogy to what described in scheme 3, step 2.

In step 4, scheme 7, the tert-butylcarbamate group of compounds 21 is removed to give the compounds of formula 22, using methods well known to someone skilled in the art, e.g. acid mediated tert-butylcarbamate deprotection. This is typically carried out with or without solvents such as dichloromethane, dioxane and tetrahydrofuran and mixtures thereof at temperature between 0° C. and 60° C. Typically used acids are hydrogen chloride, aqueous hydrochloric acid and trifluoroacetic acid.

In step 5, scheme 7, the free amino group of 5-aminomethyl-indazole-3-carboxylic acid esters 22 is reacted with a sulfonyl chloride according to methods well known to someone skilled in the art to yield the corresponding sulfonamides 23. The reaction is typically carried out in solvents such as dichloromethane, tetrahydrofuran, acetonitrile, toluene, pyridine, triethylamine, or mixtures thereof, at temperatures between 0° C. and 110° C.

In step 6, scheme 7, the ester group of compounds 23 is removed to yield the corresponding acids 24, in analogy to what described in scheme 3, step 3.

In step 7, scheme 7, the compounds of general formula VI are obtained from the acids 24 in analogy to what described in scheme 2, step 1.

The conversion of a compound of formula (I) into a pharmaceutically acceptable salt can be carried out by treatment of such a compound with an inorganic acid, for example a hydrohalic acid, such as, for example, hydrochloric acid or hydrobromic acid, or other inorganic acids such as sulfuric acid, nitric acid, phosphoric acid etc. The salts can be obtained by standard methods known to the person skilled in the art, e.g. by dissolving the compound of formula (I) in a suitable solvent such as e.g. dioxane or tetrahydrofuran and adding an appropriate amount of the corresponding acid. The products can conveniently be isolated by filtration or by chromatography. Compounds of formula (I) which comprise an acid group such as COOH or an acid isostere can form salts with physiologically compatible bases. Examples of such salts are alkaline, earth-alkaline and ammonium salts such as e.g. sodium, potassium, calcium and trimethylammonium salt. One method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoroborate (TPTU), or by direct reaction with a suitable alcohol under acidic conditions, as for example in the presence of a strong mineral acid like hydrochloric acid, sulfuric acid and the like.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

As described above, the novel compounds of the present invention have been found to inhibit liver carnitine palmitoyl transferase 1 (L-CPT1) activity. The compounds of the present invention can therefore be used in the treatment and/or prophylaxis of diseases which are modulated by L-CPT1 inhibitors, particularly diseases which are related to hyperglycemia and/or glucose tolerance disorders. Such diseases include e.g. diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by L-CPT1 inhibitors, particularly as therapeutically active substances for the treatment and/or prophylaxis of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

In another preferred embodiment, the invention relates to a method for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure, which method comprises administering a compound as defined above to a human being or animal.

The invention also embraces the use of compounds as defined above for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention also relates to the use of compounds as described above for the preparation of medicaments for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure. Such medicaments comprise a compound as described above.

Prevention and/or treatment of hyperglycemia and non insulin dependent diabetes mellitus is the preferred indication.

The following tests were carried out in order to determine the activity of the compounds of the present invention. Background information on the performed assays can be found in: Jackson et al., 1999, *Biochem. J.* 341, 483-489 and Jackson et al., 2000, *J. Biol. Chem.* 275, 19560-19566.

Human liver and muscle CPT1 cDNAs and rat CPT2 cDNA were subcloned in pGAPZB or pGAPZA, respectively. These plasmids were used to transform *P. pastoris* strain X-33 via electroporation after the preparation of electrocompetent cells. High copy number clones were selected where necessary using 0.5 or 1 mg/ml Zeocin. Cultures for activity measurements were induced for 16 h in YPD medium (1% yeast extract, 2% peptone, 2% glucose). Crude cell extracts were prepared by disrupting the cells with glass beads or French Press, depending on fermenter sizes. After centrifugation, the cell-free extracts were resuspended in cell breaking buffer (50 mM Tris, pH 7.4, 100 mM KCl, 1 mM EDTA) in the presence of a protease inhibitor cocktail, before aliquoting and freezing at −20° C.

CPT activity was measured using a spectrophotometric assay using 5,5'-dithio-bis-(2-nitrobenzoic acid) (DTNB) also called Ellman's reagent. The HS-CoA released on the formation of acylcarnitine from carnitine (500 µM) and palmitoyl-CoA (80 µM) reduced DTNB (300 µM) forming 5-mercapto-(2-nitrobenzoic acid) which absorbed at 410 nm with a molar extinction coefficient of 13600 $M^{-1} \cdot cm^{-1}$. The assay buffer contained 120 mM KCl, 25 mM Tris, pH 7.4, 1 mM EDTA. This assay was used for the identification of selective inhibitors of the liver CPT1 isoform versus the muscle CPT1 and CPT2 isoforms.

The compounds according to formula (I) preferably have an $IC_{50}$ value below 10 µM, preferably 10 nM to 10 µM, more preferably 10 nM to 5 µM. The following table shows data for some examples.

| Example | L-CPT1 inhibition $IC_{50}$ [µmol/l] |
|---|---|
| 1 | 0.26 |
| 28 | 0.6 |
| 32 | 0.026 |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-200 mg, of a compound of formula I.

The following Examples serve to illustrate the present invention in more detail. They are, however, not intended to limit its scope in any manner. The mass spectrometry terms ($ES^+$)=electro spray positive mode, and [M+H]=the molecular weight of the compound plus a proton.

EXAMPLES

Example 1

N-[1-(4-difluoromethoxy-benzyl)-1H-indazol-3-yl]-terephthalamic acid

The title compound was prepared according to the procedure illustrated in scheme 1.

Step 1. General procedure: Hydrazine monohydrate (10 equiv) was added dropwise to a stirred solution of 2-fluorobenzonitrile in ethanol (2.5 mL/mmol) at room temperature. The reaction mixture was heated under reflux for 16 hours, cooled to room temperature and concentrated in vacuo. The residue was dissolved in dichloromethane (20 mL/g), dried over magnesium sulphate and concentrated in vacuo. The material was recrystallized from ethyl acetate/heptane to give 3-aminoindazole.

Step 2. General procedure: Dimethylformamide dimethylacetal (2.0 mL/mmol) was added to 3-aminoindazole and the resulting suspension stirred at room temperature for 16 hours and then poured onto ice/water (5 volumes). The precipitate was collected by filtration, dissolved in ethyl acetate (20 mL/g), dried over magnesium sulphate and then concentrated in vacuo to afford N'-(1H-indazol-3-yl)-N,N-dimethylformamidine.

Step 3. Potassium tert-butoxide (1.4 g, 12.8 mmol) was added to a stirred solution of N'-(1H-indazol-3-yl)-N,N-dimethylformamidine (2.0 g, 10.6 mmol) in tetrahydrofuran (50 mL). 4-difluoromethoxy-benzyl bromide (3.0 g, 12.8 mmol) was then added and the reaction mixture was heated at 50° C. with stirring under an atmosphere of nitrogen for 16 hours. The reaction mixture was cooled to room temperature, water (20 mL) was added and the mixture was extracted with dichloromethane (3×20 mL). The organic layer was washed with brine (20 mL), dried over sodium sulphate and concentrated in vacuo. The crude material was purified by flash column chromatography (50% ethyl acetate/heptane) to afford N'-[1-(4-difluoromethoxybenzyl)-1H-indazol-3-yl]-N,N-dimethylformamidine, 1.08 g (30%). LC@215 nm; Rt 1.24: 95%, m/z (ES+): 345.3 (M+H).

Step 4. Hydrazine monohydrate (1.4 mL, 30.0 mmol) was added to a stirred solution of N'-[1-(4-difluoromethoxybenzyl)-1H-indazol-3-yl]-N,N-dimethylformamidine (1.1 g, 3.1 mmol) in acetonitrile (50 mL) at room temperature. The reaction mixture was heated at 60° C. for 16 hours, cooled to room temperature and then concentrated in vacuo. The residue was suspended in water (15 mL) and extracted with dichloromethane (3×15 mL). The organic layers were combined and washed with brine (15 mL), dried over sodium sulphate and concentrated in vacuo. The residue was purified by flash column chromatography (2:1 ethyl acetate/heptane) to afford 1-(4-difluoromethoxybenzyl)-1H-indazol-3-ylamine, 0.63 g (70%). LC@215 nm; Rt 1.27: 60%, m/z (ES+): 290.2 (M+H).

Step 5. A solution of 4-chlorocarbonylbenzoic acid methyl ester (0.074 g, 0.37 mmol) in acetonitrile (2.0 mL) was added to a suspension of 1-(4-difluoromethoxybenzyl)-1H-indazol-3-ylamine (0.055 g, 0.15 mmol) and Ambersep 900 carbonate resin (0.12 g, 0.45 mmol) in acetonitrile (3.0 mL). The reaction mixture was shaken at room temperature for 16 hours. Polymer supported diethylenetriamine (0.060 g, 0.45 mmol) was added to the reaction mixture and shaking continued for a further 16 hours. The reaction was filtered and concentrated in vacuo. The residue was purified by preparative HPLC to afford N-[1-(4-difluoromethoxybenzyl)-1H-indazol-3-yl]-terephthalamic acid methyl ester, 0.067 g (97%). LC@215 nm; Rt 1.55: 98%, m/z (ES+): 452.3 (M+H).

Step 6. Lithium hydroxide (0.019 g, 0.45 mmol) was added to a stirred solution of N-[1-(4-difluoromethoxybenzyl)-1H-indazol-3-yl]-terephthalamic acid methyl ester (0.067 g, 0.15 mmol) in 1:1 tetrahydrofuran/water (2.0 mL). The reaction mixture was stirred at room temperature for 6 hours then acidified with 1N HCl (1.0 mL). A precipitate was collected and dried by suction filtration to afford N-[1-(4-difluoromethoxybenzyl)-1H-indazol-3-yl]-terephthalamic acid, 0.059 g (90%). LC@215 nm; Rt 1.42: 100%, m/z (ES+): 438.1 (M+H).

Example 2

N-[1-(4-Difluoromethoxy-benzyl)-1H-indazol-3-yl]-benzamide

The title compound was prepared as described for example 1, steps 1 to 5. Step 5 was performed using benzoyl chloride. Yield 0.057 g (48%). LC@215 nm; Rt 1.55: 92%, m/z (ES+): 394.1 (M+H).

Example 3

Thiophene-2-carboxylic acid [1-(4-difluoromethoxy-benzyl)-1H-indazol-3-yl]-amide The title compound was prepared as described for example 1, steps 1 to 5. Step 5 was performed using thiophene-2-carbonyl chloride. Yield 0.050 g (42%). LC@215 nm; Rt 1.54: 100%, m/z (ES+): 400.0 (M+H).

Example 4

N-[1-(4-Difluoromethoxy-benzyl)-1H-indazol-3-yl]-3-fluoro-benzamide

The title compound was prepared as described for example 1, steps 1 to 5. Step 5 was performed using 3-fluoro-benzoyl chloride. Yield 0.058 g (47%). LC@215 nm; Rt 1.60: 92%, m/z (ES+): 412.0 (M+H).

Example 5

N-[1-(4-Difluoromethoxy-benzyl)-1H-indazol-3-yl]-3-methoxy-benzamide

The title compound was prepared as described for example 1, steps 1 to 5. Step 5 was performed using 3-methoxy-benzoyl chloride. Yield 0.050 g (40%). LC@215 nm; Rt 1.57: 100%, m/z (ES+): 424.1 (M+H).

Example 6

N-[1-(4-Difluoromethoxy-benzyl)-1H-indazol-3-yl]-isonicotinamide

The title compound was prepared as described for example 1, steps 1 to 5. Step 5 was performed using isonicotinoyl chloride. Yield 0.0044 g (4%). LC@215 nm; Rt 1.29: 100%, m/z (ES+): 395.2 (M+H).

Example 7

N-[1-(4-Difluoromethoxy-benzyl)-5-fluoro-1H-indazol-3-yl]-terephthalamic acid

The title compound was prepared as described for example 1, steps 1 to 6. Step 1 was performed using 2,5-difluoro-benzonitrile and yielded 5-fluoro-1H-indazol-3-ylamine, which was converted to N'-(5-fluoro-1H-indazol-3-yl)-N,N-dimethyl-formamidine in step 2. Step 3 was performed with 4-difluoromethoxy-benzyl bromide, yielding N'-[1-(4-difluoromethoxy-benzyl)-5-fluoro-1H-indazol-3-yl]-N,N-dimethyl-formamidine, which was deprotected to 1-(4-difluoromethoxy-benzyl)-5-fluoro-1H-indazol-3-ylamine in step 4. This was coupled to 4-chlorocarbonylbenzoic acid methyl ester in step 5 and the resulting N-[1-(4-difluoromethoxybenzyl)-5-fluoro-1H-indazol-3-yl]-terephthalamic acid methyl ester hyrdrolyzed to the title compound in step 6. Yield 0.0075 g (5%) over the two last steps. LC@215 nm; Rt 1.50: 93%, m/z (ES+): 455.9 (M+H).

Example 8

N-[1-(4-Difluoromethoxy-benzyl)-5-fluoro-1H-indazol-3-yl]-benzamide

The title compound was prepared as described for example 7, steps 1 to 5. Step 5 was performed using benzoyl chloride. Yield 0.0077 g, (6%). LC@215 nm; Rt 1.58: 95%, m/z (ES+): 412.1 (M+H).

Example 9

N-[1-(4-Difluoromethoxy-benzyl)-5-fluoro-1H-indazol-3-yl]-3-fluoro-benzamide

The title compound was prepared as described for example 7, steps 1 to 5. Step 5 was performed using 3-fluoro-benzoyl chloride. Yield 0.0092 g (7%). LC@215 nm; Rt 1.59: 98%, m/z (ES+): 430.1 (M+H).

Example 10

Thiophene-2-carboxylic acid [1-(4-difluoromethoxy-benzyl)-5-fluoro-1H-indazol-3-yl]-amide The title compound was prepared as described for example 7, steps 1 to 5. Step 5 was performed using thiophene-2-carbonyl chloride. Yield 0.0059 g (5%). LC@215 nm; Rt 1.59: 100%, m/z (ES+): 418.1 (M+H).

Example 11

N-[1-(4-Difluoromethoxy-benzyl)-5-fluoro-1H-indazol-3-yl]-3-methoxy-benzamide

The title compound was prepared as described for example 7, steps 1 to 5. Step 5 was performed using 3-methoxy-benzoyl chloride. Yield 0.0066 g (5%). LC@215 nm; Rt 1.61: 98%, m/z (ES+): 442.2 (M+H).

Example 12

N-[1-(4-Difluoromethoxy-benzyl)-5-fluoro-1H-indazol-3-yl]-isonicotinamide

The title compound was prepared as described for example 7, steps 1 to 5. Step 5 was performed using isonicotinoyl chloride. Yield 0.0056 g (5%). LC@215 nm; Rt 1.32: 95%, m/z (ES+): 413.2 (M+H).

Example 13

N-[1-(4-Difluoromethoxy-benzyl)-5-fluoro-1H-indazol-3-yl]-nicotinamide

The title compound was prepared as described for example 7, steps 1 to 5. Step 5 was performed using nicotinoyl chloride. Yield 0.0065 g (5%). LC@215 nm; Rt 1.35: 97%, m/z (ES+): 413.2 (M+H).

Example 14

N-[1-(3-Chloro-benzyl)-5-fluoro-1H-indazol-3-yl]-terephthalamic acid

The title compound was prepared as described in example 7, steps 1 to 6. Step 3 was performed with 3-chloro-benzyl bromide, yielding N'-[1-(3-chloro-benzyl)-5-fluoro-1H-indazol-3-yl]-N,N-dimethyl-formamidine, which was deprotected to 1-(3-chloro-benzyl)-5-fluoro-1H-indazol-3-ylamine in step 4. This was coupled to 4-chlorocarbonylbenzoic acid methyl ester in step 5 and the resulting N-[1-(3-chloro-benzyl)-5-fluoro-1H-indazol-3-yl]-terephthalamic acid methyl ester hydrdolyzed to the title compound in step 6. Yield 0.0059 g (5%) over the last two steps. LC@215 nm; Rt 1.51: 88%, m/z (ES+): 423.9 (M+H).

Example 15

N-[1-(3-Chloro-benzyl)-5-fluoro-1H-indazol-3-yl]-benzamide

The title compound was prepared as described in example 14, steps 1 to 5. Step 5 was performed using benzoyl chloride. Yield 0.0075 g (7%). LC@215 nm; Rt 1.62: 93%, m/z (ES+): 380.1 (M+H).

Example 16

N-[1-(3-Chloro-benzyl)-5-fluoro-1H-indazol-3-yl]-3-fluoro-benzamide

The title compound was prepared as described in example 14, steps 1 to 5. Step 5 was performed using 3-fluoro-benzoyl chloride. Yield 0.0074 g (6%). LC@215 nm; Rt 1.63: 96%, m/z (ES+): 398.1 (M+H).

Example 17

N-[1-(3-Chloro-benzyl)-5-fluoro-1H-indazol-3-yl]-3-methoxy-benzamide

The title compound was prepared as described in example 14, steps 1 to 5. Step 5 was performed using 3-methoxy-benzoyl chloride. Yield 0.011 g (9%). LC@215 nm; Rt 1.64: 95%, m/z (ES+): 410.1 (M+H).

Example 18

Thiophene-2-carboxylic acid [1-(3-chloro-benzyl)-5-fluoro-1H-indazol-3-yl]-amide The title compound was prepared as described in example 14, steps 1 to 5. Step 5 was performed using thiophene-2-carbonyl chloride. Yield 0.0046 g (4%). LC@215 nm; Rt 1.62: 100%, m/z (ES+): 386.1 (M+H).

Example 19

Furan-2-carboxylic acid [1-(3-chloro-benzyl)-5-fluoro-1H-indazol-3-yl]-amide

The title compound was prepared as described in example 14, steps 1 to 5. Step 5 was performed using furan-2-carbonyl chloride. Yield 0.0048 g (4%). LC@215 nm; Rt 1.54: 98%, m/z (ES+): 370.1 (M+H).

Example 20

N-[1-(4-Difluoromethoxy-benzyl)-7-fluoro-1H-indazol-3-yl]-terephthalamic acid

The title compound was prepared as described for example 1, steps 1 to 6. Step 1 was performed using 2,3-difluorobenzonitrile and yielded 7-fluoro-1H-indazol-3-ylamine, which was protected to N'-(7-fluoro-1H-indazol-3-yl)-N,N-dimethyl-formamidine in step 2. Step 3 was performed using 4-difluoromethoxy-benzyl bromide, and yielded N'-[1-(4-difluoromethoxy-benzyl)-7-fluoro-1H-indazol-3-yl]-N,N-dimethyl-formamidine, which was deprotected to 1-(4-difluoromethoxy-benzyl)-7-fluoro-1H-indazol-3-ylamine in step 4. This was coupled to 4-chlorocarbonylbenzoic acid methyl ester in step 5 and the resulting N-[1-(4-difluoromethoxy-benzyl)-7-fluoro-1H-indazol-3-yl]-terephthalamic acid methyl ester was hydrdolyzed to the title compound in step 6. Yield 0.004 g (3%) over the two last steps. LC@215 nm; Rt 1.50: 97%, m/z (ES+): 456.1 (M+H).

Example 21

N-[1-(3-Chloro-benzyl)-7-fluoro-1H-indazol-3-yl]-terephthalamic acid

The title compound was prepared as in example 20, steps 1 to 6. Step 3 was performed with 3-chloro-benzyl bromide, yielding N'-[1-(3-chloro-benzyl)-7-fluoro-1H-indazol-3-yl]-N,N-dimethyl-formamidine, which was deprotected to 1-(3-chloro-benzyl)-7-fluoro-1H-indazol-3-ylamine in step 4. This was coupled to 4-chlorocarbonylbenzoic acid methyl ester in step 5 and the resulting N-[1-(3-chloro-benzyl)-7-fluoro-1H-indazol-3-yl]-terephthalamic acid methyl ester hydrdolyzed to the title compound in step 6. Yield 0.0032 g (3%) over the two last steps. LC@215 nm; Rt 1.52: 86%, m/z (ES+): 424.1 (M+H).

Example 22

Thiophene-2-carboxylic acid [1-(3-chloro-benzyl)-7-fluoro-1H-indazol-3-yl]-amide The title compound was prepared as in example 21, step 1 to 5. Step 5 was performed using thiophene-2-carbonyl chloride. Yield 0.0036 g (3%). LC@215 nm; Rt 1.71: 97%, m/z (ES+): 386.1 (M+H).

Example 23

N-[1-(3-Chloro-benzyl)-6-fluoro-1H-indazol-3-yl]-terephthalamic acid

The title compound was prepared as described for example 1, steps 1 to 6. Step 1 was performed using 2,4-difluoro-benzonitrile and yielded 6-fluoro-1H-indazol-3-ylamine, which was protected to N'-(6-fluoro-1H-indazol-3-yl)-N,N-dimethyl-formamidine in step 2. Step 3 was performed using 3-chloro-benzyl bromide, and yielded N'-[1-(3-chloro-benzyl)-6-fluoro-1H-indazol-3-yl]-N,N-dimethyl-formamidine, which was deprotected to 1-(3-chloro-benzyl)-6-fluoro-1H-indazol-3-ylamine in step 4. This was coupled to 4-chlorocarbonylbenzoic acid methyl ester in step 5 and the resulting N-[1-(3-chloro-benzyl)-6-fluoro-1H-indazol-3-yl]-terephthalamic acid methyl ester was hydrdolyzed to the title compound in step 6. Yield 0.0016 g (1%) over the two last steps. LC@215 nm; Rt 1.50: 86%, m/z (ES+): 424.1 (M+H).

Example 24

Thiophene-2-carboxylic acid [1-(4-difluoromethoxy-benzyl)-6-fluoro-1H-indazol-3-yl]-amide The title compound was prepared as in example 23, steps 1 to 5. Step 3 was performed with 4-difluoromethoxy-benzyl bromide, yielding N'-[1-(4-difluoromethoxy-benzyl)-6-fluoro-1H-indazol-3-yl]-N,N-dimethyl-formamidine, which was deprotected to 1-(4-difluoromethoxy-benzyl)-6-fluoro-1H-indazol-3-ylamine in step 4. This was coupled to thiophene-2-carbonyl chloride in step 5. Yield 0.0038 g (3%). LC@215 nm; Rt 1.59: 98%, m/z (ES+): 418.1 (M+H).

Example 25

Thiophene-2-carboxylic acid (1-benzyl-1H-indazol-3-yl)-amide

The title compound was prepared as described for example 1, steps 1 to 5. Step 3 was performed using benzyl bromide, yielding N'-(1-benzyl-1H-indazol-3-yl)-N,N-dimethyl-formamidine, which was deprotected to 1-benzyl-1H-indazol-3-ylamine in step 4. This was coupled to thiophene-2-carbonyl chloride in step 5. Yield 0.056 g (56%). LC@215 nm; Rt 1.47: 100%, m/z (ES+): 334.1 (M+H).

Example 26

1-ethyl-5-(3-propyl-ureido)-1H-indazole-3-carboxylic acid (thiophen-2-ylmethyl)-amide The title compound was prepared according to the procedure illustrated in schemes 3 and 6.

Step 1. Iodoethane (11.6 mL, 145 mmol) was added to a suspension of 5-nitro-1H-indazole-3-carboxylic acid (10.0 g, 48 mmol) and $K_2CO_3$ (20.3 g, 145 mmol) in dimethylformamide (100 mL). The reaction mixture was shaken at room temperature for 18 hours. Again, iodoethane (11.6 mL, 145 mmol) and $K_2CO_3$ (20.3 g, 145 mmol) were added to the reaction mixture and shaken for another 18 hours, then heated at 80° C. for a further 18 hours. The reaction mixture was saturated with water (300 mL) and extracted with dichloromethane (3×300 mL). The organic phases were combined and washed with brine (300 mL), dried over magnesium sulphate and concentrated in vacuo. The residue was purified by flash column chromatography (10% to 50% ethyl acetate/heptane) to afford 1-ethyl-5-nitro-1H-indazole-3-carboxylic acid ethyl ester, 4.45 g (35%). LC@215 nm; Rt 1.41: 94%, m/z (ES+): 264.2 (M+H).

Step 2. Lithium hydroxide (2.5 g, 59.6 mmol) was added to a solution of 1-ethyl-5-nitro-1H-indazole-3-carboxylic acid ethyl ester (3.8 g, 14.4 mmol) in a 1:1 mixture of tetrahydrofuran/water (60 mL). The reaction mixture was shaken for 18 hours. The reaction mixture was acidified to pH 1 with concentrated HCl and extracted with ethyl acetate (3×50 mL). The combined organic layers were dried over magnesium sulphate and concentrated in vacuo. The resultant solid was suspended in toluene and the solvent was evaporated to afford 1-ethyl-5-nitro-1H-indazole-3-carboxylic acid, 3.85 g (97%). LC@215 nm; Rt 1.08: 100%, m/z (ES+): 236.2 (M+H).

Step 3. Pentafluorophenyltrifluoroacetate (1.85 mL, 10.8 mmol) was added dropwise to a solution of 1-ethyl-5-nitro-1H-indazole-3-carboxylic acid (1.59 g, 6.77 mmol) in 1:1 mixture of tetrahydrofuran/pyridine (16 mL) at 0° C. The reaction mixture was allowed to warm up to room temperature and was shaken for 16 hours. The solution was concentrated in vacuo and the residue was taken up in ethyl acetate (50 mL). The solution was washed with 0.1 N HCl (3×40 mL) followed by a saturated sodium bicarbonate solution (40 mL). The organic layer was dried over magnesium sulphate and concentrated in vacuo. The residue was dissolved in dimethylformamide (16 mL) and triethylamine (1.3 mL, 9.36 mmol) to which thiophene-2-methylamine (1.16 g, 10.2 mmol) was added. The reaction mixture was shaken at room temperature for 16 hours then diluted with dichloromethane (50 mL) and washed 1N HCl (3×40 mL) and brine (3×40 mL). The organic layer was dried over magnesium sulphate and concentrated in vacuo. The residue was recrystallized from dichloromethane to afford 1-ethyl-5-nitro-1H-indazole-3-carboxylic acid (thiophen-2-ylmethyl)-amide, 1.67 g (75%). LC@215 nm; Rt 1.45: 96%, m/z (ES+): 331.3 (M+H).

Step 4. 1N HCl (2.0 mL) was added to a suspension of iron powder (3.0 g) and 1-ethyl-5-nitro-1H-indazole-3-carboxylic acid (thiophen-2-ylmethyl)-amide (1.67 g, 5.37 mmol) in a 1:1 mixture of ethanol/water (15 mL). The reaction mixture was heated at 80° C. for 8 hours, then cooled to room temperature, filtered through Celite® and concentrated in vacuo. The residue was dissolved in ethyl acetate (20 mL) and washed with 1N HCl (3×10 mL), followed by saturated sodium bicarbonate (10 mL). The organic layer was dried over magnesium sulphate and concentrated in vacuo. The residue was purified by flash column chromatography (20% to 50% ethyl acetate/heptane) to afford 5-amino-1-ethyl-1H-indazole-3-carboxylic acid (thiophen-2-ylmethyl)-amide, 0.44 g (29%). LC@215 nm; Rt 1.03: 88%, m/z (ES+): 301.3 (M+H).

Step 5. Propyl isocyanate (0.011 g, 0.13 mmol) was added to a solution of 5-amino-1-ethyl-1H-indazole-3-carboxylic acid (thiophen-2-ylmethyl)-amide (0.027 g, 0.089 mmol in dichloroethane (2.0 mL). The reaction mixture was shaken at room temperature for 16 hours then concentrated in vacuo. The residue was purified by preparative HPLC to afford 1-ethyl-5-(3-propyl-ureido)-1H-indazole-3-carboxylic acid (thiophen-2-ylmethyl)-amide, 0.0099 g (29%). LC@215 nm; Rt 1.38: 92%, m/z (ES+): 386.4 (M+H).

Example 27

1-Ethyl-5-(3-isopropyl-ureido)-1H-indazole-3-carboxylic acid (thiophen-2-ylmethyl)-amide The title compound was prepared as described in example 26, steps 1 to 5. Step 5 was performed using isopropyl isocyanate. Yield 0.014 g (42%). LC@215 nm; Rt 1.37: 97%, m/z (ES+): 386.4 (M+H).

Example 28

1-Ethyl-5-(3-phenethyl-ureido)-1H-indazole-3-carboxylic acid (thiophen-2-ylmethyl)-amide The title compound was prepared as described in example 26, steps 1 to 5. Step 5 was performed using phenethyl isocyanate. Yield 0.011 g (27%). LC@215 nm; Rt 1.51: 97%, m/z (ES+): 448.4 (M+H).

Example 29

N-[1-Ethyl-5-(3-ethyl-ureido)-1H-indazol-3-yl]-2-thiophen-2-yl-acetamide

The title compound was prepared as described in example 26, steps 1 to 5. Step 5 was performed using ethyl isocyanate. Yield 0.017 g (51%). LC@215 nm; Rt 1.30: 97%, m/z (ES+): 372.3 (M+H).

Example 30

1-(4-Nitro-benzyl)-1H-indazole-3-carboxylic acid (pyridin-3-ylmethyl)-amide

The title compound was prepared according to the procedure illustrated in scheme 3. Step 1. A solution of indazole-3-carboxylic acid (10.0 g, 61.7 mmol) in tetrahydrofuran (150 mL) was treated with carbonyldiimidazole (10.5 g, 64.7 mmol). The mixture was warmed to reflux and stirred for 4 hours. 2-Trimethylsilanyl-ethanol (9.70 mL, 67.8 mmol) was added and the mixture was warmed at reflux for further 10 hours. A further aliquot of 2-trimethylsilanyl-ethanol (7.0 mL, 49 mmol) was added and the mixture stirred at reflux for 24 hours. The mixture was quenched with water (20 mL) and part of the solvent was evaporated. The residual slurry was partitioned between water and diethyl ether. The organic phase was washed three times with water, then with saturated $NH_4Cl$ and water. The organic phase was then dried with sodium sulphate and evaporated. The residue was suspended in hexane and sonicated, and the precipitate was filtered off, yielding crude 1H-indazole-3-carboxylic acid 2-trimethylsilanyl-ethyl ester, 12.6 g (77.8%), which was used crude.

Step 2. A solution of 1H-indazole-3-carboxylic acid 2-trimethylsilanyl-ethyl ester (3.50 g, 13.3 mmol) in dimethylformamide (50 mL) was treated with 4-nitro-benzyl chloride (2.40 g, 14.0 mmol). The resulting solution was cooled to 0° C. and sodium hydride (55% in mineral oil, 0.750 g, 17.3 mmol) was added in four portions. After stirring for 10 min at 0° C., the mixture was left to warm to room temperature and stirred for 20 hours. The mixture was partitioned between diethyl ether and a 10% $KHSO_4$ solution. The organic phase was separated and washed with water and brine, dried over magnesium sulphate and evaporated. The residue was purified by flash chromatography (heptane/dichloromethane gradient), yielding 1-(4-nitro-benzyl)-1H-indazole-3-carboxylic acid 2-trimethylsilanyl-ethyl ester as a yellow amorphous solid, 1.53 g (29%), m/z (ISP): 370.1 (M+H).

Step 3. A solution of 1-(4-nitro-benzyl)-1H-indazole-3-carboxylic acid 2-trimethylsilanyl-ethyl ester (1.24 g, 3.12 mmol) in tetrahydrofuran (35 mL) was cooled to 0° C. and treated with a solution of tetrabutylammonium fluoride monohydrate (1.20 g, 3.75 mmol) in tetrahydrofuran (15 mL). The mixture was stirred at room temperature for 1 hour. After cooling back to 0° C., again a solution of tetrabutylammonium fluoride monohydrate (0.79 g, 2.5 mmol) in tetrahydrofuran (10 mL) was added dropwise. The mixture was stirred for one further hour at room temperature, then partitioned between diethyl ether and a 10% $KHSO_4$ solution. The organic phase was separated and washed with water and brine, dried over magnesium sulphate and evaporated. Crude 1-(4-nitro-benzyl)-1H-indazole-3-carboxylic acid was obtained as a yellow solid, 0.99 g (100%), m/z (ISP): 296.5 (M−H).

Step 4. A solution of 1-(4-nitro-benzyl)-1H-indazole-3-carboxylic acid (0.15 g, 0.50 mmol) in dichloromethane (4.0 mL) was treated at room temperature with pyridin-3-yl-methylamine (0.055 g, 0.50 mmol), 1-(3-dimethylaminopropyl)-3-ethyl-carbodiimide hydrochloride (0.12 g, 0.61 mmol) and 4-dimethylamino-pyridine (0.092 g, 0.76 mmol). The mixture was stirred at room temperature for 2 hours. The solvent was evaporated and the residue purified by flash chromatography (heptane/ethyl acetate gradient) to yield 1-(4- nitro-benzyl)-1H-indazole-3-carboxylic acid (pyridin-3-ylmethyl)-amide as a light yellow solid, 0.033 g (17%), m/z (ISP): 388.0 (M+H).

Example 31

1-(4-Difluoromethoxy-benzyl)-1H-indazole-3-carboxylic acid (thiophen-2-ylmethyl)-amide The title compound was prepared according to the procedure illustrated in scheme 2.

Step 1. A solution of indazole-3-carboxylic acid (1.50 g, 9.25 mmol) in dimethylformamide (70 mL) was treated with thiophene-2-ylmethyl-amine (1.57 g, 13.9 mmol), diisopropylethyl amine (3.59 g, 4.70 mL, 27.8 mmol) and O-(benzotriazol-1-yl)-N,N,N',N'-tetramethyluronium hexafluorophosphate (4.46 g, 13.9 mmol.). The mixture was stirred at room temperature for 16 hours, then diluted with water. The resulting slurry was extracted three times with ethyl acetate. The combined organic phases were dried with sodium sulphate and evaporated. The residue was suspended in dichloromethane and sonicated. The precipitated was filtered and dried under vacuum to afford 1H-indazole-3-carboxylic acid (thiophen-2-ylmethyl)-amide, 1.46 g (61%), m/z (ISP): 256.0 (M−H).

Step 2. A solution of 1H-indazole-3-carboxylic acid (thiophen-2-ylmethyl)-amide (0.030 g, 0.12 mmol) in tetrahydrofuran (0.44 mL) was treated with a solution of potassium tert-butylate (0.13 mmol) in tetrahydrofuran (0.40 mL). The mixture was stirred at 60° C. for 30 min, then treated with a solution of 4-difluoromethoxy-benzyl bromide (0.034 g, 0.14 mmoL) in tetrahydrofuran (0.40 mL). The mixture was stirred at 60° C. for 3 h, then the volatiles were evaporated. The residue was redissolved in acetonitrile and purified by preparative HPLC (Column: Zorbax Eclipse XBD-C18, 21.2×50 mm, 5 um, PN 970050-902, SN USDN001065. Gradient: 0-0.5 min: 10% acetonitrile in (water+0.1% HCO$_2$H), 0.5-2.4 min: increasing of acetonitrile from 10% to 95%, 2.4-4.75 min: 95% of acetonitrile, 4.75-4.8 min: decreasing acetonitrile from 95% to 10%. Program end at 5 min. Flow: 30 mL/min) to yield 1-(4-difluoromethoxy-benzyl)-1H-indazole-3-carboxylic acid (thiophen-2-ylmethyl)-amide, 0.036 g (73%), m/z (ISP): 414.1 (M+H).

Example 32

1-(3-Trifluoromethyl-benzyl)-1H-indazole-3-carboxylic acid (thiophen-2-ylmethyl)-amide The title compound was obtained as described for example 32, using 3-trifluoromethyl-benzyl bromide in step 2. Yield 0.036 g (73%), m/z (ES+): 416.0 (M+H).

Example 33

4-({[1-(4-Difluoromethoxy-benzyl)-5-fluoro-1H-indazole-3-carbonyl]-amino}-methyl)-benzoic acid The title compound was prepared as illustrated in scheme 3 and 5.

Step 1. A solution of 5-fluoro-isatin (10.0 g, 60.6 mmol) in 1N NaOH (61 mL) was stirred at 60° C. for 20 min. The solution was cooled to 3° C. and a solution of sodium nitrite (4.59 g, 66.6 mmol) in water (20 mL) was added, and the mixture stirred for 20 min. The resulting solution was added dropwise to a cooled solution of concentrated sulfuric acid (3.64 ml, 67.9 mmol) in water (130 mL) so that the temperature remained between 0 and 4° C. The mixture was stirred at 0-5° C. for 2 h, then added portionwise to a solution of SnCl$_2$ (22.0 g, 116 mmol) in concentrated HCl (46 mL). The mixture was left for 5 hours, upon which crystallization took place. The crystals were filtered off, washing with water, to yield 5-fluoro-1H-indazole-3-carboxylic acid as a white solid (9.76 g). The raw material was then dissolved in tetrahydrofuran (100 mL) and treated with carbonyldiimidazole (CDI, 9.82 g, 60.6 mmol). The mixture was warmed to reflux and stirred for 2 hours. EtOH (100 mL) was then added, and the mixture stirred at reflux for further 5 hours. The volatiles were evaporated and the residue redissolved in warm ethyl acetate. The organic solution was washed with 1N HCl, and then with water, dried with sodium sulphate and evaporated. The raw material was purified by flash chromatography (heptane/ethyl acetate 1:1, followed by a second chromatography with dichloromethane/diethyl ether 9:1) to yield 5-fluoro-1H-indazole-3-carboxylic acid ethyl ester as an off-white solid, 6.22 g (49.3%).

Step 2. A solution of 5-fluoro-1H-indazole-3-carboxylic acid ethyl ester (2.50 g, 12.0 mmol) in dimethylformamide (30 mL) was treated with 4-difluoromethoxy-benzyl chloride (2.59 g, 13.2 mmol). The resulting solution was cooled to 0° C. and sodium hydride (55% in mineral oil, 0.680 g, 15.6 mmol) was added in three portions. After stirring for 10 min at 0° C., the mixture was left to warm to room temperature and stirred for 2 hours. The mixture was partitioned between diethyl ether and a 10% KHSO$_4$ solution. The organic phase was separated and washed with water and brine, dried over magnesium sulphate and evaporated. The residue was purified by flash chromatography (heptane/ethyl acetate gradient), yielding 1-(4-difluoromethoxy-benzyl)-5-fluoro-1H-indazole-3-carboxylic acid ethyl ester as a yellow crystalline solid, 1.76 g (40%), m/z (ISP): 365.0 (M+H).

Step 3. A solution of 1-(4-difluoromethoxy-benzyl)-5-fluoro-1H-indazole-3-carboxylic acid ethyl ester (1.68 g, 4.61 mmol) in tetrahydrofuran (20.0 mL) was treated with a 1N solution of lithium hydroxide at 0° C. The mixture was stirred at 0° C. for 15 min, then at room temperature for 3 hours and at 50° C. for 4 hours. After cooling to room temperature, the mixture was acidified with HCl 1N (14 mL) and extracted with ethyl acetate. The combined organic phases were dried over magnesium sulphate and evaporated. The residue was suspended in heptane and the precipitate was filtered and dried under vacuum. 5-Fluoro-1H-indazole-3-carboxylic acid was obtained as a yellow solid, 1.5 g (97%), m/z (ISP): 335.2 (M−H).

Step 4. A solution of 5-fluoro-1H-indazole-3-carboxylic acid (0.25 g, 0.74 mmol) in dichloromethane (5.0 mL) was treated with triethylamine (0.083 g, 0.11 mL, 0.82 mmol), 4-dimethylamino pyridine (0.14 g, 1.1 mmol) and 1-(3-dimethylaminopropyl)-3-ethyl-carbodiimide hydrochloride (0.17 g, 0.89 mmol). 4-Aminomethyl-benzoic acid methyl ester (0.16 g, 0.82 mmol) was added. The mixture was stirred at room temperature for 16 hours, then partitioned between diethyl ether and 1N HCl. The organic phase was washed with water and brine, dried over magnesium sulphate and evaporated. The residue was purified by flash chromatography (heptane/ethyl acetate gradient), to yield 4-({[1-(4-difluoromethoxy-benzyl)-5-fluoro-1H-indazole-3-carbonyl]-amino}-methyl)-benzoic acid methyl ester as a yellow solid, 0.19 g (54%), m/z (ISP): 484.5 (M+H).

Step 5. 4-({[1-(4-Difluoromethoxy-benzyl)-5-fluoro-1H-indazole-3-carbonyl]-amino}-methyl)-benzoic acid methyl ester (0.16 g, 0.32 mmol) was dissolved in tetrahydrofuran (2.0 mL) and treated at 0° C. with 1N LiOH. The mixture was stirred at room temperature for 3 hours, then at 50° C. for 5 hours. After cooling back to room temperature, the reaction mixture was acidified with 1N HCl (1.0 mL) and extracted with ethyl acetate. The organic phase was dried over magnesium sulphate and evaporated. The residue was suspended in a heptane/diethyl ether mixture and the precipitate filtered to yield 4-({[1-(4-difluoromethoxy-benzyl)-5-fluoro-1H-indazole-3-carbonyl]-amino}-methyl)-benzoic acid as an off-white solid, 0.13 g (89%), m/z (ISP): 468.0 (M−H).

Example 34

(2-{[1-(4-Difluoromethoxy-benzyl)-5-fluoro-1H-indazole-3-carbonyl]-amino}-thiazol-4-yl)-acetic acid The title compound was prepared as illustrated for example 33, steps 1 to 5. Step 4 was performed using 2-amino-thiazol-4-yl)-acetic acid ethyl ester, yielding (2-{[1-(4-difluoromethoxy-benzyl)-5-fluoro-1H-indazole-3-carbonyl]-amino}-thiazol-4-yl)-acetic acid ethyl ester, which was hydrdolyzed to the title compound in step 5. Yield 0.045 g (72%), m/z (ISP): 475.1 (M−H).

Example 35

1-(4-Difluoromethoxy-benzyl)-5-fluoro-1H-indazole-3-carboxylic acid [4-(1H-tetrazol-5-yl)-phenyl]-amide;

The title compound was prepared as illustrated for example 33, steps 1 to 4. Step 4 was performed using 4-(1H-tetrazol-5-yl)-phenylamine hydrochloride. Yield 0.027 g (13%), m/z (ISP): 480.0 (M+H).

4-(1H-Tetrazol-5-yl)-phenylamine hydrochloride was prepared as described below: A solution of 4-aminobenzonitrile (5.00 g, 42.3 mmol) in dichloromethane (50 mL) was treated with di-tert-butyl dicarbonate (9.52 g, 42.3 mmol) and dimethylaminopyridine (0.300 g, 2.46 mmol) and heated at reflux for 20 h. Further di-tert-butyl dicarbonate (2.00 g, 9.16 mmol) was added, and the mixture refluxed for further 10 h. Another aliquot of di-tert-butyl dicarbonate (1.00 g, 4.08 mmol) was added and the mixture refluxed for further 18 h. The mixture was partitioned between ethyl acetate and 1N NH₄Cl. The organic phase was separated and washed with water, then dried with magnesium sulphate and evaporated, yielding crude (4-cyano-phenyl)-carbamic acid tert-butyl ester (11.0 g). The raw material was dissolved in dimethylformamide (100 mL) and treated with NaN$_3$ (8.25 g, 127 mmol) and NH₄Cl (6.79 g, 127 mmol). The mixture was warmed at 140° C. and stirred for 4 h. The mixture was then partitioned between diethyl diethyl ether and 1N HCl. The organic phase was separated and washed with water, then dried with magnesium sulphate and evaporated. The residue was taken up in diethyl diethyl ether and filtered, to afford crude [4-(1H-tetrazol-5-yl)-phenyl]-carbamic acid tert-butyl ester as an off-white solid (7.30 g).

The raw material (4.55 g) was then dissolved in dioxane (25 mL) and treated with a 4N solution of HCl in dioxane (75 mL). The mixture was stirred at room temperature for 20 h, then the volatiles evaporated and the residue dried under high vacuum. The title compound was obtained as an off-white crystalline solid, 4.0 g (76%).

Example 36

1-(4-Difluoromethoxy-benzyl)-5-fluoro-1H-indazole-3-carboxylic acid 4-(1H-tetrazol-5-yl)-benzylamide The title compound was prepared as illustrated for example 33, steps 1 to 4. Step 4 was performed using 4-(1H-tetrazol-5-yl)-benzylamine hydrochloride. Yield 0.041 g (19%), m/z (ISP): 494.4 (M+H).

4-(1H-Tetrazol-5-yl)-benzylamine hydrochloride was prepared in analogy to what described in example 35 for the synthesis of 4-(1H-tetrazol-5-yl)-phenylamine hydrochloride, using 4-aminomethyl-benzonitrile (10 g, 75.7 mmol) as starting material. 4-(1H-Tetrazol-5-yl)-benzylamine hydrochloride was obtained as an off-white crystalline solid, 17.5 g (94%).

Example 37

(4-{[1-(4-Difluoromethoxy-benzyl)-5-fluoro-1H-indazole-3-carbonyl]-amino}-2-methyl-phenoxy)-acetic acid The title compound was prepared as illustrated for example 33, steps 1 to 5. Step 4 was performed using (4-amino-2-methyl-phenoxy)-acetic acid methyl ester, yielding (4-{[1-(4-difluoromethoxy-benzyl)-5-fluoro-1H-indazole-3-carbonyl]-amino}-2-methyl-phenoxy)-acetic acid methyl ester which was hydrdolyzed to the title compound in step 5. Yield 0.095 g (50%), m/z (ISP): 500.3 (M+H).

Example 38

1-(4-Difluoromethoxy-benzyl)-5-fluoro-1H-indazole-3-carboxylic acid [4-(5-oxo-4,5-dihydro-[1,2,4]oxadiazol-3-yl)-phenyl]-amide The title compound was prepared as illustrated for example 33, steps 1 to 4. Step 4 was performed using 3-(4-amino-phenyl)-4H-[1,2,4]oxadiazol-5-one. Yield 0.11 g (57%), m/z (ISP): 494.0 (M−H).

3-(4-Amino-phenyl)-4H-[1,2,4]oxadiazol-5-one was prepared as follows:

Crude (4-cyano-phenyl)-carbamic acid tert-butyl ester (see example 35) (3.00 g, 13.7 mmol) was dissolved in methanol (30 mL) and treated with hydroxylamine hydrochloride (1.91 g, 27.5 mmol) and sodium hydrogenocarbonate (2.31 g, 27.5 mmol). The mixture was warmed to reflux for 4 hours, then the volatiles were evaporated. The residue was taken up in diethyl ether and the solution was washed with water, saturated sodium hydrogenocarbonate and brine, dried over magnesium sulphate and evaporated.

Part of the crude residue (0.502 g) was dissolved in tetrahydrofuran (10 mL) and treated with carbonyl diimidazole (0.42 g, 2.6 mmol). The mixture was heated at reflux for 2 hours, then partitioned between ethyl acetate and 1N HCl. The organic phase was dried over magnesium sulphate and evaporated. The crude (0.45 g) was dissolved in a 4N solution of HCl in dioxane (10 mL) and stirred at room temperature for 20 hours. The volatiles were evaporated to yield 3-(4-aminophenyl)-4H-[1,2,4]oxadiazol-5-one as an off-white solid, 0.35 g (99% crude yield), which was used crude.

Example 39

4-{[5-Fluoro-1-(3-trifluoromethyl-benzyl)-1H-indazole-3-carbonyl]-amino}-benzoic acid The title compound was prepared as illustrated in example 33, steps 1 to 5. Step 2 was performed using 3-trifluoromethyl-benzyl chloride, and yielded 1-(3-trifluoromethyl-benzyl)-5-fluoro-1H-indazole-3-carboxylic acid ethyl ester, which was hydrdolyzed to 1-(3-trifluoromethyl-benzyl)-5-fluoro-1H-indazole-3-carboxylic acid in step 3. This was coupled to 4-amino-benzoic acid ethyl ester in step 4, and the resulting 4-{[5-fluoro-1-(3-trifluoromethyl-benzyl)-5-fluoro-1H-indazole-3-carbonyl]-amino}-benzoic acid ethyl ester was hydrdolyzed to the title compound in step 5. Yield over the last two steps 0.087 g, (41%), m/z (ISP): 458.5 (M+H).

Example 40

5-Fluoro-1-(3-trifluoromethyl-benzyl)-1H-indazole-3-carboxylic acid [4-(1H-tetrazol-5-yl)-phenyl]-amide The title compound was prepared as example 39, steps 1 to 4. Step 4 was performed using 4-(1H-tetrazol-5-yl)-phenylamine hydrochloride (see example 35). Yield 0.015 g (7%), m/z (ISP): 480.1 (M−H).

Example 41

5-Fluoro-1-(3-trifluoromethyl-benzyl)-1H-indazole-3-carboxylic acid 4-(1H-tetrazol-5-yl)-benzylamide The title compound was prepared as example 39, steps 1 to 4. Step 4 was performed using 4-(1H-tetrazol-5-yl)-benzylamine hydrochloride (see example 36). Yield 0.034 g (16%), m/z (ISP): 494.4 (M−H).

Example 42

1-(4-Carbamoyl-benzyl)-1H-indazole-3-carboxylic acid 4-(1H-tetrazol-5-yl)-benzylamide The title compound was prepared as follows:
Step 1. 1H-indazole-3-carboxylic acid ethyl ester (2.00 g, 10.5 mmol) was dissolved in acetonitrile (20.0 mL) and treated with cesium carbonate (4.45 g, 11.0 mmol) and 4-bromomethyl benzonitrile (2.20 g, 11.0 mmol). The mixture was stirred at room temperature for 2 hours, then diluted with dimethylformamide (10 mL) and stirred for further 16 hours. The mixture was partitioned between diethyl ether and water and the organic phase was washed with 1N HCl (30 mL), water and brine, dried over magnesium sulphate and evaporated. The residue was purified by flash chromatography (heptane/ethyl acetate gradient) to yield 1-(4-cyano-benzyl)-1H-indazole-3-carboxylic acid ethyl ester as a light yellow solid, 1.94 g (60%), m/z (ISP): 306.3 (M+H).

Step 2. 1-(4-cyano-benzyl)-1H-indazole-3-carboxylic acid ethyl ester (0.80 g, 2.6 mmol) was taken up in concentrated sulfuric acid and warmed to 50° C. After 30 min at 50° C., the mixture was poured over ice and the resulting slurry extracted with ethyl acetate. The organic phase was washed with water and brine until neutral pH, dried over magnesium sulphate and evaporated. The residue was suspended in heptane and the precipitate filtered to yield 1-(4-carbamoyl-benzyl)-1H-indazole-3-carboxylic acid ethyl ester as a colorless solid, 0.79 g (93%), m/z (ISP): 324.4 (M+H).

1-(4-Carbamoyl-benzyl)-1H-indazole-3-carboxylic acid ethyl ester was further processed in analogy to example 33, steps 3 and 4. The compound was hydrdolyzed to 1-(4-carbamoyl-benzyl)-1H-indazole-3-carboxylic acid in step 3 and coupled to 4-(1H-tetrazol-5-yl)-benzylamine hydrochloride (see example 36) in step 4 to yield the title compound. Yield 0.114 g (26%) over the last two steps, m/z (ISP): 453.3 (M+H).

Example 43

1-(4-Carbamoyl-benzyl)-5-fluoro-1H-indazole-3-carboxylic acid 4-(1H-tetrazol-5-yl)-benzylamide The title compound was prepared as follows:
1-(4-Cyano-benzyl)-5-fluoro-1H-indazole-3-carboxylic acid 4-(1H-tetrazol-5-yl)-benzylamide (0.17 g, 0.37 mmol) was taken up in concentrated sulfuric acid and stirred at room temperature for 6 hours. The mixture was poured over ice and the resulting suspension was filtered, washing the precipitate with water. The filtrated was dried under vacuum to yield the title compound as a light yellow solid, 0.063 g (36%), m/z (ISP): 471.4 (M+H).

1-(4-Cyano-benzyl)-5-fluoro-1H-indazole-3-carboxylic acid 4-(1H-tetrazol-5-yl)-benzylamide was prepared in analogy to example 33, steps 1 to 4. Step 2 was performed with 4-bromomethyl benzonitrile, yielding 1-(4-cyano-benzyl)-5-fluoro-1H-indazole-3-carboxylic acid ethyl ester, which was hydrdolyzed to 1-(4-cyano-benzyl)-5-fluoro-1H-indazole-3-carboxylic acid in step 3. This was coupled to 4-(1H-tetrazol-5-yl)-benzylamine hydrochloride (see example 36) in step 4, to yield 1-(4-cyano-benzyl)-5-fluoro-1H-indazole-3-carboxylic acid 4-(1H-tetrazol-5-yl)-benzylamide as a light yellow solid. Yield 0.203 g (53%), m/z (ISP): 453.1 (M+H).

Example 44

1-(5-Chloro-2-methoxy-benzyl)-5-fluoro-3-[4-(1H-tetrazol-5-yl)-phenylsulfanylmethyl]-1H-indazole The title compound was prepared according to what illustrated in schemes 3 and 4.

Step 1. A solution of 5-fluoro-1H-indazole-3-carboxylic acid ethyl ester (see example 33) (1.70 g, 8.30 mmol) in dimethylformamide (25 mL) was treated with 4-chloro-2-chloromethyl-1-methoxy-benzene (1.75 g, 9.10 mmol) and cooled to 0° C. Sodium hydride (55% suspension in mineral oil, 0.470 g, 10.8 mmol) was added in portions over 10 min. After stirring for 15 min at 0° C., the mixture was left to warm to room temperature and stirred for 16 hours. The reaction mixture was partitioned between diethyl ether and 1N HCl (30 mL). The organic phase was washed with water and brine until neutral, dried with magnesium sulphate and evaporated. The residue was purified by flash chromatography (heptane/ethyl acetate gradient) to yield 1-(5-chloro-2-methoxy-benzyl)-5-fluoro-1H-indazole-3-carboxylic acid ethyl ester as a yellow solid, 2.1 g (70%), m/z (ISP): 363.3 (M+H).

Step 2. 1-(5-Chloro-2-methoxy-benzyl)-5-fluoro-1H-indazole-3-carboxylic acid ethyl ester (1.2 g, 3.3 mmol) was dissolved in tetrahydrofuran (15 mL) and the solution cooled to −75° C. A 1.2 M solution of diisobutylaluminium hydride in toluene (9.10 mL, 10.9 mmol) was added within 15 min, so that the temperature did not exceed −67° C. The mixture was then stirred at room temperature for 1 hour. After cooling to 0° C., the reaction was quenched with 2N HCl (11 mL), and stirred vigorously for 15 min. The resulting slurry was extracted with diethyl ether. The combined organic phases were washed with water and brine until neutral pH, dried over magnesium sulphate and evaporated. The residue was purified by flash chromatography (heptane/ethyl acetate gradient) to yield [1-(5-chloro-2-methoxy-benzyl)-5-fluoro-1H-indazol-3-yl]-methanol as a yellow, crystalline solid, 0.83 g (78%), m/z (ISP): 321.0 (M+H).

Step 3. A solution of [1-(5-chloro-2-methoxy-benzyl)-5-fluoro-1H-indazol-3-yl]-methanol (0.78 g, 2.4 mmol) in dichloromethane (8.0 mL) was treated at 0° C. with thionyl chloride (0.23 mL, 3.2 mmol). After stirring at 0° C. for 10 min, the mixture was warmed to room temperature and stirred for 1 hour. The mixture was partitioned between water and dichloromethane, the organic phase was dried with magnesium sulphate and evaporated. The residual crystalline solid was crude 1-(5-chloro-2-methoxy-benzyl)-3-chloromethyl-5-fluoro-1H-indazole, which was used as such. Yield 0.81 g (98%), m/z (ISP): 339.1 (M+H).

Step 4. 1-(5-Chloro-2-methoxy-benzyl)-3-chloromethyl-5-fluoro-1H-indazole (0.2 g, 0.6 mmol) was dissolved in acetonitrile (3.0 mL) and treated with 4-mercapto-benzonitrile (0.080 g, 0.60 mmol) and cesium carbonate (0.27 g, 0.80 mmol). After 10 min, the suspension was diluted with dimethylformamide (1.0 mL). The mixture was stirred at room temperature for 16 hours, then partitioned between diethyl ether and water. The organic phase was washed with water and brine, dried over magnesium sulphate and evaporated. The residue was suspended in diethyl ether and the precipitate filtered and dried under high vacuum to yield 4-[1-(5-chloro-2-methoxy-benzyl)-5-fluoro-1H-indazol-3-ylmethylsulfanyl]-benzonitrile as a white solid, 0.16 g (63%), m/z (ISP): 438.1 (M+H).

Step 5. 4-[1-(5-Chloro-2-methoxy-benzyl)-5-fluoro-1H-indazol-3-ylmethylsulfanyl]-benzonitrile (0.14 g, 0.30 mmol) was dissolved in dimethylformamide (1.0 mL) and treated with ammonium chloride (0.050 g, 0.95 mmol) and sodium azide (0.060 g, 0.95 mmol). The mixture was warmed to 140° C. and stirred for 24 hours. After cooling to room temperature, the reaction mixture was treated with 1N HCl and stirred for 20 min. The slurry was diluted with acetone and extracted with diethyl ether. The organic phase was washed with water and brine, dried over magnesium sulphate and evaporated. The residue was purified by flash chromatography (dichloromethane/methanol gradient) to yield 1-(5-chloro-2-methoxy-benzyl)-5-fluoro-3-[4-(1H-tetrazol-5-yl)-phenylsulfanylmethyl]-1H-indazole as a light yellow solid, 0.009 g (6%), m/z (ISP): 481.2 (M+H).

4-Chloro-2-chloromethyl-1-methoxy-benzene, used in step 1, was prepared as follows: A cooled (0° C.) solution of (5-chloro-2-methoxy-phenyl)-methanol (4.54 g, 26.3 mmol) in dichloromethane (50 mL) was treated with thionyl chloride (2.01 mL, 27.7 mmol), which was added dropwise over 10 min. The mixture was stirred at room temperature for 16 h, then partitioned between diethyl ether and water. The organic phase was dried with sodium sulphate and evaporated. The residue was pure 4-chloro-2-chloromethyl-1-methoxy-benzene, 4.93 g (98%), and was used as such.

Example 45

1-(4-Difluoromethoxy-benzyl)-1H-indazole-3,6-dicarboxylic acid 6-amide 3-[4-(1H-tetrazol-5-yl)-benzylamide]

The title compound was prepared as follows:
6-Cyano-1-(4-difluoromethoxy-benzyl)-1H-indazole-3-carboxylic acid 4-(1H-tetrazol-5-yl)-benzylamide (0.077 g, 0.15 mmol) was dissolved in tetrahydrofuran (0.6 mL) and ethanol (0.6 mL) and treated with a 1N solution of LiOH (0.6 mL, 0.6 mmol). The mixture was stirred at 50° C. for 9 hours, then quenched with 1N HCl (0.65 mL). The resulting suspension was filtered washing with water and the residue dried under vacuum to yield the title compound as a light yellow solid, 0.034 g (43%), m/z (ISP): 519.3 (M+H).

6-Cyano-1-(4-difluoromethoxy-benzyl)-1H-indazole-3-carboxylic acid 4-(1H-tetrazol-5-yl)-benzylamide was prepared in analogy to example 33, steps 2 to 4. Step 2 was performed using 6-cyano-1H-indazole-3-carboxylic acid ethyl ester (prepared from 6-cyano indole according to the method described in J. Med. Chem. 1997, 2843) and yielded 6-cyano-1-(4-difluoromethoxy-benzyl)-1H-indazole-3-carboxylic acid ethyl ester, which was hydrdolyzed to 6-cyano-1-(4-difluoromethoxy-benzyl)-1H-indazole-3-carboxylic acid in step 3. This was coupled to 4-(1H-tetrazol-5-yl)-benzylamine hydrochloride (see example 36) in step 4, to yield 6-cyano-1-(4-difluoromethoxy-benzyl)-1H-indazole-3-carboxylic acid 4-(1H-tetrazol-5-yl)-benzylamide as a colorless solid. Yield 0.083 g (38%), m/z (ISP): 501.2 (M+H).

Example 46

1-(4-Difluoromethoxy-benzyl)-6-(methanesulfonylamino-methyl)-1H-indazole-3-carboxylic acid [4-(1H-tetrazol-5-yl)-phenyl]-amide The title compound was prepared as illustrated in scheme 7.

Step 1. A suspension of 6-cyano-1H-indazole-3-carboxylic acid ethyl ester (J. Med. Chem. 1997, 2843) (2.50 g, 11.6 mmol) in ethanol (50 mL) and chloroform (2.5 mL) was treated with platinum oxide. The flask was evacuated and filled with hydrogen. The mixture was stirred at room temperature for 2 hours. Methanol (30 mL) was added, and the mixture was stirred for further 28 hours. The solids were filtered, and the filtrate evaporated. The raw material was purified by trituration in diethyl ether to yield 6-aminomethyl-1H-indazole-3-carboxylic acid ethyl ester hydrochloride as a brown crystalline solid, 2.45 g (96%). m/z (ISP): 220.3 (M+H$^+$); $^1$H NMR: $\delta_H$ (300 MHz; CDCl$_3$): 14.20 (1H, s); 8.54 (3H, bs); 8.08 (1H, d); 7.84 (1H, s); 7.45 (1H, d); 4.40 (2H, q); 4.20 (2H, s); 1.38 (3H, t).

Step 2. A solution of 6-aminomethyl-1H-indazole-3-carboxylic acid ethyl ester hydrochloride (1.2 g, 4.9 mmol) in dichloromethane (30 mL) was treated with triethylamine (1.50 g, 14.7 mmol) and a solution of di-tert-butyl dicarbonate (1.15 g, 5.10 mmol) in dimethylformamide (10 mL). The mixture was stirred at room temperature for 1 hour. The reaction mixture was partitioned between diethyl ether and 1N HCl. The organic phase was washed with water and brine until neutral pH, dried over magnesium sulphate and evaporated. The residue was purified by flash chromatography (heptane/ethyl acetate gradient) to yield 6-(tert-butoxycarbonylamino-methyl)-1H-indazole-3-carboxylic acid ethyl ester as a crystalline white solid, 0.99 g (63%), m/z (ISP): 320.1 (M+H).

Step 3. 6-(tert-Butoxycarbonylamino-methyl)-1H-indazole-3-carboxylic acid ethyl ester (0.94 g, 2.9 mmol) was reacted with 4-difluoromethoxy-benzyl bromide in analogy to example 42, step 1. 6-(tert-Butoxycarbonylamino-methyl)-1-(4-difluoromethoxy-benzyl)-1H-indazole-3-carboxylic acid ethyl ester was obtained as a crystalline white solid, 0.74 g (53%), m/z (ISP): 476.3 (M+H).

Step 4. 6-(tert-Butoxycarbonylamino-methyl)-1-(4-difluoromethoxy-benzyl)-1H-indazole-3-carboxylic acid ethyl ester (0.2 g, 0.4 mmol) was dissolved in a 4N solution of HCl in dioxane (2.0 mL) and stirred at room temperature for 30 min. The volatiles were evaporated to yield crude 6-aminomethyl-1-(4-difluoromethoxy-benzyl)-1H-indazole-3-carboxylic acid ethyl ester hydrochloride as a white crystalline solid, 0.17 g (100%), m/z (ISP): 376.1 (M+H).

Step 5. A solution of 6-aminomethyl-1-(4-difluoromethoxy-benzyl)-1H-indazole-3-carboxylic acid ethyl ester hydrochloride (0.16 g, 0.40 mmol) in dichloromethane (2.0 mL) was cooled to 0° C. and treated with triethylamine (0.064 g, 0.63 mmol) and methanesulfonyl chloride (0.064 g, 0.44 mmol). The mixture was stirred at 0° C. for 15 min, then at room temperature for 45 min. A further aliquot of triethylamine (0.087 g) was added and the mixture stirred for further 45 min. The mixture was partitioned between ethyl acetate and 1N HCl. The organic phase was washed with water and brine until neutral pH, then dried over magnesium sulphate and evaporated. The residue was crude 1-(4-difluoromethoxy-benzyl)-6-(methanesulfonylamino-methyl)-1H-indazole-3-carboxylic acid ethyl ester, 0.18 g (96%), m/z (ISP): 454.4 (M+H).

Step 6. 1-(4-Difluoromethoxy-benzyl)-6-(methanesulfonylamino-methyl)-1H-indazole-3-carboxylic acid ethyl ester (0.18 g, 0.4 mmol) was hydrdolyzed in analogy to example 33, step 4. 1-(4-Difluoromethoxy-benzyl)-6-(methanesulfonylamino-methyl)-1H-indazole-3-carboxylic acid was obtained as a crystalline white solid, 0.17 g (100%), m/z (ISP): 426.0 (M+H).

Step 7. 1-(4-Difluoromethoxy-benzyl)-6-(methanesulfonylamino-methyl)-1H-indazole-3-carboxylic acid (0.08 g, 0.2 mmol) was coupled to 4-(1H-tetrazol-5-yl)-phenylamine hydrochloride in analogy to example 33, step 4. 1-(4-Difluoromethoxy-benzyl)-6-(methanesulfonylamino-methyl)-1H-indazole-3-carboxylic acid [4-(1H-tetrazol-5-yl)-phenyl]-amide was obtained as a yellow crystalline solid, 0.053 g (49%), m/z (ISP): 567.2 (M−H).

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Polyvinylpyrrolidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A compound of formula (I):

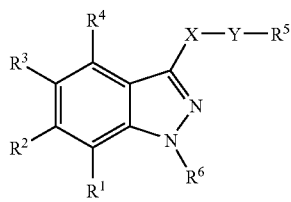

or a pharmaceutically acceptable salt or ester thereof, wherein:

X is —NH—C(O)—;

Y is —$(CR^9R^{10})_n$—, wherein $R^9$ and $R^{10}$ independently from each other are selected from the group consisting of hydrogen, lower alkyl, fluoro-lower-alkyl, lower-alkoxy, and fluoro-lower-alkoxy; and n is 0 or 1;

$R^1$, $R^2$, $R^3$ and $R^4$ independently from each other are selected from the group consisting of:
(1) hydrogen,
(2) halogen,
(3) lower-alkyl,
(4) fluoro-lower-alkyl,
(5) lower-alkoxy,
(6) fluoro-lower-alkoxy,
(7) carbamoyl,
(8) lower-alkyl-NH—C(O)—NH,
(9) aryl-lower-alkyl-NH—C(O)—NH, and
(10) lower-alkyl-$SO_2$—NH-lower-alkyl;

$R^5$ is phenyl or a heteroaryl selected from the group consisting of (a) thiophenyl, (b) pyridinyl, (c) furanyl, and (d) thiazolyl, which phenyl or heteroaryl is optionally substituted with 1 to 3 substituents independently selected from the group consisting of:
(1) halogen,
(2) lower-alkyl,
(3) fluoro-lower-alkyl,
(4) lower-alkoxy,
(5) fluoro-lower-alkoxy,
(6) hydroxy,
(7) HO—$SO_2$,
(8) $NH_2$—$SO_2$,
(9) N(H,lower-alkyl)-$SO_2$,
(10) N(lower-alkyl)$_2$-$SO_2$,
(11) lower-alkyl-$SO_2$—NH,
(12) carboxy,
(13) carboxy-lower-alkyl,
(14) carboxy-lower-alkoxy,
(15) $NO_2$,
(16) CN,
(17) $NH_2$,
(18) N(H,lower-alkyl),
(19) N(lower-alkyl)$_2$,
(20) $NH_2C(O)$,
(21) N(H,lower-alkyl)C(O),
(22) N(lower-alkyl)$_2$C(O),
(23) lower-alkyl-C(O)NH,
(24) 1H-tetrazol-5-yl, and
(25) 5-oxo-4,5-dihydro-[1,2,4]oxadiazol-3-yl;

$R^6$ is

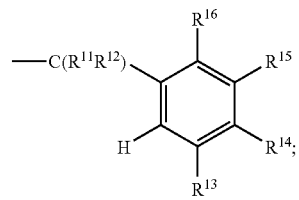

wherein: (a) $R^{11}$ and $R^{12}$ independently from each other are selected from the group consisting of hydrogen, lower-alkyl, fluoro-lower-alkyl, lower-alkoxy, and fluoro-lower-alkoxy; (b) $R^{13}$, $R^{14}$ and $R^{15}$ independently from each other are selected from the group consisting of hydrogen, lower-alkyl, halogen, fluoro-lower-alkyl, lower-alkoxy, hydroxy, fluoro-lower-alkoxy, $NO_2$ and $NH_2$—C(O); and (c) $R^{16}$ is hydrogen or lower-alkoxy;

with the proviso that the compound of formula (I) is not:
N-[1-(phenylmethyl)-1H-indazol-3-yl]-benzamide,
4-methyl-N-[1-(phenylmethyl)-1H-indazol-3-yl]-benzamide,
4-nitro-N-[1-(phenylmethyl)-1H-indazol-3-yl]-benzamide,
4-chloro-N-[1-(phenylmethyl)-1H-indazol-3-yl]-benzamide,
4-methoxy-N-[1-(phenylmethyl)-1H-indazol-3-yl]-benzamide,
N-[1-(phenylmethyl)-1H-indazol-3-yl]-benzenacetamide, or
N-(1-ethyl-1H-indazol-3-yl)-benzamide.

2. A compound of claim 1, wherein $R^1$, $R^2$, $R^3$ and $R^4$ independently from each other are selected from the group consisting of: hydrogen, halogen, carbamoyl, lower-alkyl-NH—C(O)—NH, aryl-lower-alkyl-NH—C(O)—NH, and lower-alkyl-$SO_2$—NH-lower-alkyl.

3. A compound of claim 1, wherein $R^1$, $R^2$, $R^3$ and $R^4$ independently from each other are hydrogen or halogen.

4. A compound of claim 1, wherein $R^1$, is hydrogen.

5. A compound of claim 1, wherein $R^2$ is hydrogen.

6. A compound of claim 1, wherein $R^3$ is hydrogen or fluoro.

7. A compound of claim 1, wherein $R^4$ is hydrogen.

8. A compound of claim 1, wherein $R^5$ is phenyl or heteroaryl selected from the group consisting of thiophenyl, pyridinyl, furanyl and thiazolyl, which phenyl or heteroaryl is optionally substituted with 1 to 3 substituents independently selected from the group consisting of halogen, lower-alkyl, lower-alkoxy, carboxy, carboxy-lower-alkyl, carboxy-lower-alkoxy, 1H-tetrazol-5-yl, and 5-oxo-4,5-dihydro-[1,2,4]oxadiazol-3-yl.

9. A compound of claim 1, wherein $R^5$ is phenyl or thiophenyl, which phenyl or thiophenyl is optionally substituted with 1 to 3 substituents independently selected from the group consisting of halogen, lower-alkoxy, carboxy and 1H-tetrazol-5-yl.

10. A compound of 1, wherein $R^5$ is 4-carboxy-phenyl, thiophenyl, phenyl, 3-fluoro-phenyl, 3-methoxy-phenyl, or 4-(1H-tetrazol-5-yl)-phenyl.

11. A compound of claim 1, wherein $R^6$ is

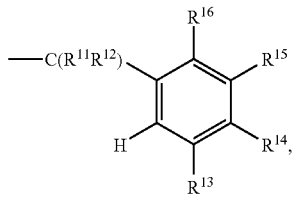

wherein $R^{11}$ and $R^{12}$ are hydrogen and $R^{13}$, $R^{14}$, $R^{15}$ and $R^{16}$ are as defined in claim 1.

12. A compound of claim 1, wherein n is 0.

13. A compound of claim 1, wherein $R^{13}$, $R^{14}$ and $R^{15}$ independently from each other are selected from the group consisting of hydrogen, halogen, fluoro-lower-alkyl, fluoro-lower-alkoxy, and $NH_2$—C(O).

14. A compound of claim 1, wherein: (a) $R^{13}$ is hydrogen, trifluoromethyl or chloro; and (b) $R^{14}$ is hydrogen, difluoromethoxy or $NH_2$—C(O).

15. A compound of claim 1, wherein $R^{15}$ is hydrogen and $R^{16}$ is hydrogen.

16. A compound of claim 1, selected from the group consisting of:
N-[1-(4-Difluoromethoxy-benzyl)-1H-indazol-3-yl]-terephthalamic acid,
N-[1-(4-Difluoromethoxy-benzyl)-1H-indazol-3-yl]-benzamide,
Thiophene-2-carboxylic acid [1-(4-difluoromethoxy-benzyl)-1H-indazol-3-yl]-amide,
N-[1-(4-Difluoromethoxy-benzyl)-1H-indazol-3-yl]-3-fluoro-benzamide,
N-[1-(4-Difluoromethoxy-benzyl)-1H-indazol-3-yl]-3-methoxy-benzamide,
N-[1-(4-Difluoromethoxy-benzyl)-1H-indazol-3-yl]-isonicotinamide,
N-[1-(4-Difluoromethoxy-benzyl)-5-fluoro-1H-indazol-3-yl]-terephthalamic acid,
N-[1-(4-Difluoromethoxy-benzyl)-5-fluoro-1H-indazol-3-yl]-benzamide,
N-[1-(4-Difluoromethoxy-benzyl)-5-fluoro-1H-indazol-3-yl]-3-fluoro-benzamide,
Thiophene-2-carboxylic acid [1-(4-difluoromethoxy-benzyl)-5-fluoro-1H-indazol-3-yl]-amide;
and any pharmaceutically acceptable salt or ester thereof.

17. A compound of claim 1, selected from the group consisting of:
N-[1-(4-Difluoromethoxy-benzyl)-5-fluoro-1H-indazol-3-yl]-3-methoxy-benzamide,
N-[1-(4-Difluoromethoxy-benzyl)-5-fluoro-1H-indazol-3-yl]-isonicotinamide,
N-[1-(4-Difluoromethoxy-benzyl)-5-fluoro-1H-indazol-3-yl]-nicotinamide,
N-[1-(3-Chloro-benzyl)-5-fluoro-1H-indazol-3-yl]-terephthalamic acid,
N-[1-(3-Chloro-benzyl)-5-fluoro-1H-indazol-3-yl]-benzamide,
N-[1-(3-Chloro-benzyl)-5-fluoro-1H-indazol-3-yl]-3-fluoro-benzamide,
N-[1-(3-Chloro-benzyl)-5-fluoro-1H-indazol-3-yl]-3-methoxy-benzamide,
Thiophene-2-carboxylic acid [1-(3-chloro-benzyl)-5-fluoro-1H-indazol-3-yl]-amide,
Furan-2-carboxylic acid [1-(3-chloro-benzyl)-5-fluoro-1H-indazol-3-yl]-amide,
N-[1-(4-Difluoromethoxy-benzyl)-7-fluoro-1H-indazol-3-yl]-terephthalamic acid,
and any pharmaceutically acceptable salt or ester thereof.

18. A compound of claim 1, selected from the group consisting of:
N-[1-(3-Chloro-benzyl)-7-fluoro-1H-indazol-3-yl]-terephthalamic acid,
Thiophene-2-carboxylic acid [1-(3-chloro-benzyl)-7-fluoro-1H-indazol-3-yl]-amide,
N-[1-(3-Chloro-benzyl)-6-fluoro-1H-indazol-3-yl]-terephthalamic acid,
Thiophene-2-carboxylic acid [1-(4-difluoromethoxy-benzyl)-6-fluoro-1H-indazol-3-yl]-amide,
Thiophene-2-carboxylic acid (1-benzyl-1H-indazol-3-yl)-amide, amide,
and any pharmaceutically acceptable salt or ester thereof.

19. A compound of claim 1, selected from the group consisting of:
N-[1-(4-Difluoromethoxy-benzyl)-1H-indazol-3-yl]-terephthalamic acid,
N-[1-(4-Difluoromethoxy-benzyl)-5-fluoro-1H-indazol-3-yl]-terephthalamic acid,
N-[1-(4-Difluoromethoxy-benzyl)-5-fluoro-1H-indazol-3-yl]-benzamide,
N-[1-(4-Difluoromethoxy-benzyl)-5-fluoro-1H-indazol-3-yl]-3-fluoro-benzamide,
Thiophene-2-carboxylic acid [1-(4-difluoromethoxy-benzyl)-5-fluoro-1H-indazol-3-yl]-amide,
N-[1-(4-Difluoromethoxy-benzyl)-5-fluoro-1H-indazol-3-yl]-3-methoxy-benzamide,
N-[1-(3-Chloro-benzyl)-5-fluoro-1H-indazol-3-yl]-terephthalamic acid,
Thiophene-2-carboxylic acid [1-(3-chloro-benzyl)-5-fluoro-1H-indazol-3-yl]-amide,
and any pharmaceutically acceptable salt or ester thereof.

20. A pharmaceutical composition comprising a therapeutically effective amount of a compound of claim 1 and a pharmaceutically acceptable carrier.

* * * * *

UNITED STATES PATENT AND TRADEMARK OFFICE
CERTIFICATE OF CORRECTION

PATENT NO. : 7,858,645 B2
APPLICATION NO. : 11/875025
DATED : December 28, 2010
INVENTOR(S) : Jean Ackermann et al.

Page 1 of 1

It is certified that error appears in the above-identified patent and that said Letters Patent is hereby corrected as shown below:

Claim 18, column 46, line 36, delete "amide, amide," and insert -- amide, --

Signed and Sealed this
Eighth Day of March, 2011

David J. Kappos
*Director of the United States Patent and Trademark Office*